United States Patent
Taniguchi

(10) Patent No.: US 9,204,781 B2
(45) Date of Patent: Dec. 8, 2015

(54) IMAGE PROCESSING APPARATUS AND IMAGE PROCESSING METHOD

(71) Applicant: OLYMPUS MEDICAL SYSTEMS CORP., Tokyo (JP)

(72) Inventor: Katsuyoshi Taniguchi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 76 days.

(21) Appl. No.: 14/221,978

(22) Filed: Mar. 21, 2014

(65) Prior Publication Data

US 2014/0303435 A1 Oct. 9, 2014

Related U.S. Application Data

(63) Continuation of application No. PCT/JP2013/077612, filed on Oct. 10, 2013.

(30) Foreign Application Priority Data

Oct. 18, 2012 (JP) .................................. 2012-231182

(51) Int. Cl.
  *A61B 1/00* (2006.01)
  *A61B 1/04* (2006.01)
  *G06T 7/00* (2006.01)

(52) U.S. Cl.
  CPC ............ *A61B 1/00009* (2013.01); *A61B 1/0002* (2013.01); *A61B 1/0005* (2013.01);
  (Continued)

(58) Field of Classification Search
  CPC ............ A61B 1/00009; A61B 1/00006; A61B 1/0002; A61B 1/00045; A61B 1/0005; A61B 1/041; G06T 7/0016; G06T 2207/10068; G06T 2207/30028
  See application file for complete search history.

(56) References Cited

U.S. PATENT DOCUMENTS 8,164,672 B2 * 4/2012 Meron et al. ............. 348/333.05
8,167,789 B2 * 5/2012 Sato et al. ...................... 600/109
(Continued)

FOREIGN PATENT DOCUMENTS

JP  2005-288043 A  10/2005
JP  2008-237640 A  10/2008
(Continued)

OTHER PUBLICATIONS

International Search Report dated Nov. 26, 2013 from related International Application No. PCT/JP2013/077612.

*Primary Examiner* — John P Leubecker
(74) *Attorney, Agent, or Firm* — Scully, Scott, Murphy & Presser, PC

(57) ABSTRACT

A image processing apparatus includes an image extraction unit that extracts first and second feature images representing first and second feature, respectively from a first image group acquired by sequentially capturing images of inside of a subject, and that further extracts third and fourth feature images representing first and second feature, respectively from a second image group acquired before the first image group, a feature data acquiring unit that acquires first and second feature data characterizing a movement of the capsule endoscope between the first and second feature images and between the third and the fourth feature images, respectively, a comparing unit that compares the first feature data with the second feature data, and a display control unit that performs, with respect to the first image group, display control based on a result of the comparison by the comparing unit.

13 Claims, 17 Drawing Sheets

(52) U.S. Cl.
CPC ......... *A61B1/00006* (2013.01); *A61B 1/00045* (2013.01); *A61B 1/041* (2013.01); *G06T 7/0016* (2013.01); *A61B 1/00016* (2013.01); *G06T 2207/10068* (2013.01); *G06T 2207/30028* (2013.01)

(56) References Cited

U.S. PATENT DOCUMENTS

| | | | |
|---|---|---|---|
| 8,194,096 B2 * | 6/2012 | Hirakawa et al. | 345/619 |
| 8,353,816 B2 | 1/2013 | Shimizu et al. | |
| 8,413,079 B2 | 4/2013 | Oda | |
| 8,562,515 B2 | 10/2013 | Nishino | |
| 8,900,124 B2 * | 12/2014 | Hirakawa | 600/109 |
| 2005/0075551 A1 * | 4/2005 | Horn et al. | 600/361 |
| 2010/0083178 A1 * | 4/2010 | Zui et al. | 715/823 |
| 2010/0097392 A1 * | 4/2010 | Nishiyama et al. | 345/593 |

FOREIGN PATENT DOCUMENTS

| | | |
|---|---|---|
| JP | 2009-5866 A | 1/2009 |
| JP | 2009-213627 A | 9/2009 |
| WO | WO 2010109726 A1 * | 9/2010 |

* cited by examiner

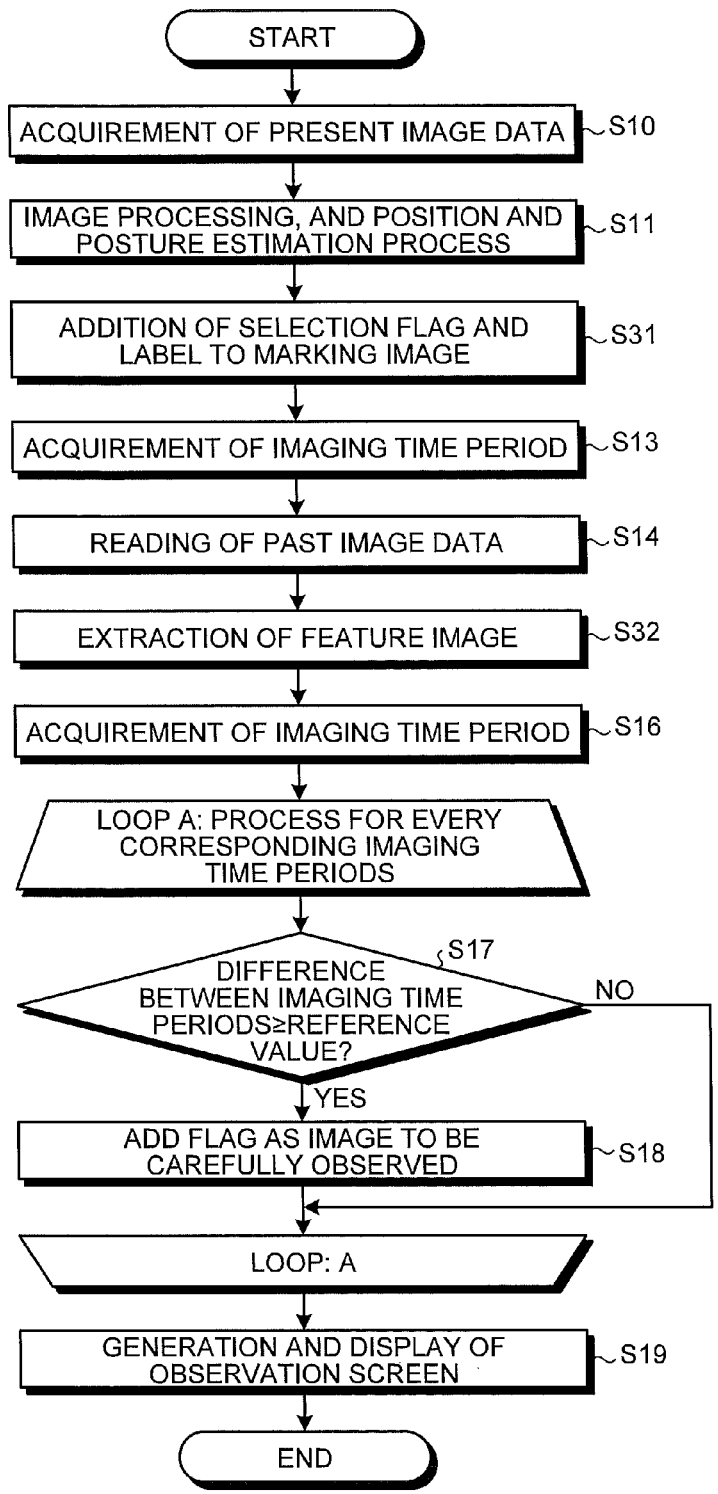

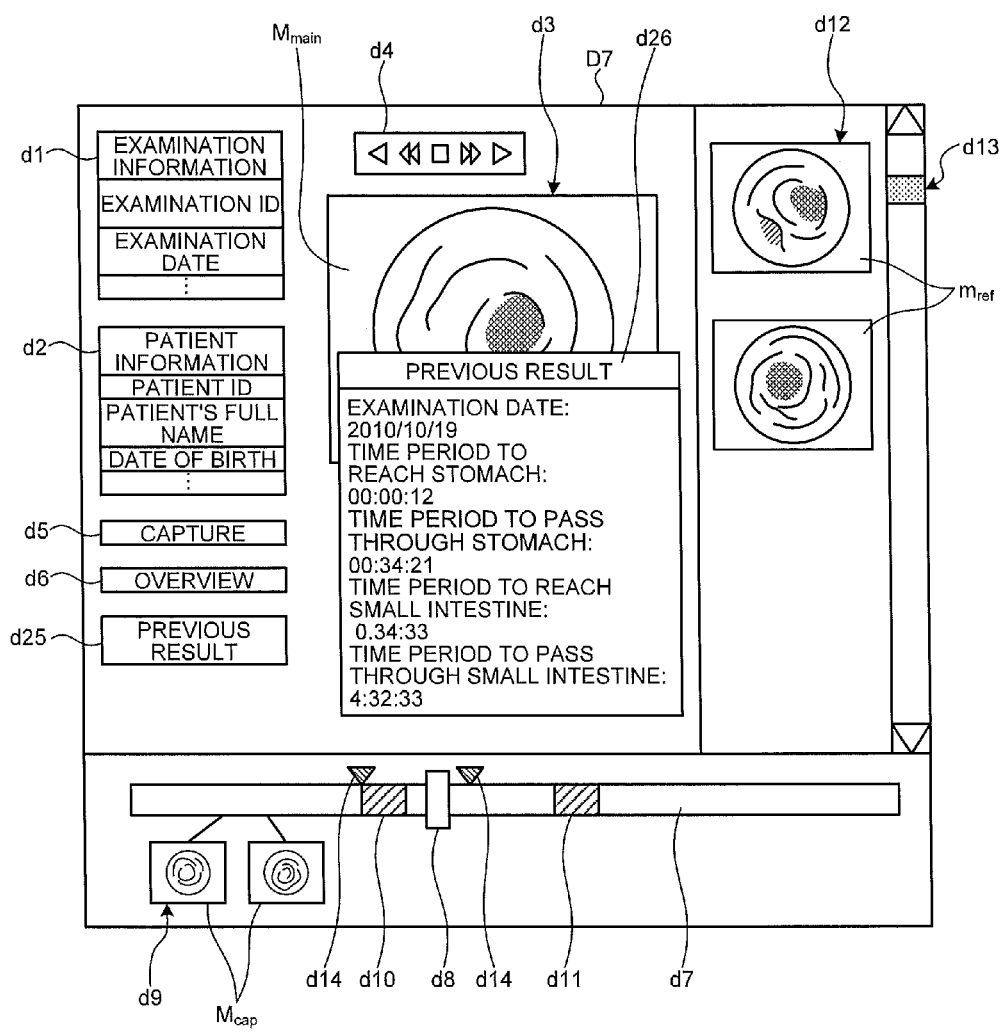

IMAGE PROCESSING APPARATUS AND IMAGE PROCESSING METHOD

CROSS REFERENCES TO RELATED APPLICATIONS

This application is a continuation of PCT international application Ser. No. PCT/JP2013/077612 filed on Oct. 10, 2013 which designates the United States, incorporated herein by reference, and which claims the benefit of priority from Japanese Patent Applications No. 2012-231182, filed on Oct. 18, 2012, incorporated herein by reference.

BACKGROUND OF THE INVENTION

1. Field of the Invention

The present invention relates to an image processing apparatus and an image processing method, which process images acquired by a capsule endoscope that is introduced into a subject and captures images of inside of the subject.

2. Description of the Related Art

In recent years, examinations using capsule endoscopes that are introduced into subjects such as patients and capture images of inside of the subjects are known in the field of endoscopes. A capsule endoscope is an apparatus that has built-in imaging function, wireless communication function, and the like, which are in a casing of a capsule shape that is formed into a size introducible into a digestive tract of a subject, and sequentially, the capsule endoscope wirelessly transmits image data generated by capturing images of inside of the subject to outside of the subject. The series of image data wirelessly transmitted from the capsule endoscope are once accumulated in a receiving device provided outside of the subject, are transferred to (downloaded by) an image processing apparatus such as a work station from the receiving device, and are subjected to various image processing in the image processing apparatus. Thereby, a series of images, in which an organ or the like in the subject is photographed, are generated.

These images are displayed on a screen in a format of a pseudo moving image, a list of still images or the like. A medical worker (medical doctor) performs diagnosis on the subject by observing the images displayed on the screen and selecting those with an abnormality.

One examination using the capsule endoscope takes about eight hours and the images acquired during that period of time amount to about 60,000 images. Therefore, to observe all of these images takes a very long time and requires an ability to concentrate. Accordingly, in the image processing apparatus, in order to aid the work of observation, an abnormal part extraction function, which is for automatically extracting images considered to have a medical abnormality, for example, like images having high red components, is available. This abnormal part extraction function is realized generally by collecting images determined by medical workers to have a medical abnormality and incorporating software, which has an algorithm of extracting images with feature data similar to those images, into hardware such as a work station.

As a technique related to display of images acquired by examinations, for example, in Japanese Patent Application Laid-open No. 2005-288043, a medical image diagnosis apparatus is disclosed, which displays, together on a same screen, diagnosis images being captured in real time at a medical diagnosis apparatus, such as a CT apparatus, an MR apparatus, an ultrasonic wave diagnosis apparatus, or the like and diagnosis images that have been captured in the past.

SUMMARY OF THE INVENTION

An image processing apparatus according to one aspect of the present invention is an image processing apparatus that processes an image of inside of a subject, the image acquired by a capsule endoscope that is introduced into the subject and captures images of the inside of the subject, including: an image extraction unit that extracts, from a first image group acquired by sequentially capturing images of the inside of the subject by the capsule endoscope, a first feature image representing a first feature and a second feature image representing a second feature, and that further extracts, from a second image group acquired before the first image group by sequentially capturing images of the inside of the subject, a third feature image representing the first feature and a fourth feature image representing the second feature; a feature data acquiring unit that acquires a first feature data characterizing a movement of the capsule endoscope between the first feature image and the second feature image extracted from the first image group, and a second feature data characterizing a movement of the capsule endoscope between the third feature image and the fourth feature image extracted from the second image group; a comparing unit that compares the first feature data with the second feature data; and a display control unit that performs, with respect to the first image group, display control based on a result of the comparison by the comparing unit.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 16 is a flow chart illustrating operations of the image processing apparatus illustrated in FIG. 15; and FIG. 17 is a schematic diagram illustrating a display example of an observation screen according to a modified example 4 of the first to third embodiments of the present invention.

DETAILED DESCRIPTION OF THE PREFERRED EMBODIMENTS

Hereinafter, image processing apparatuses and image processing methods according to embodiments of the present invention will be described with reference to the drawings. The present invention is not limited by these embodiments. Further, in describing the drawings, the same portions are appended with the same reference signs.

First Embodiment

Figure 1:
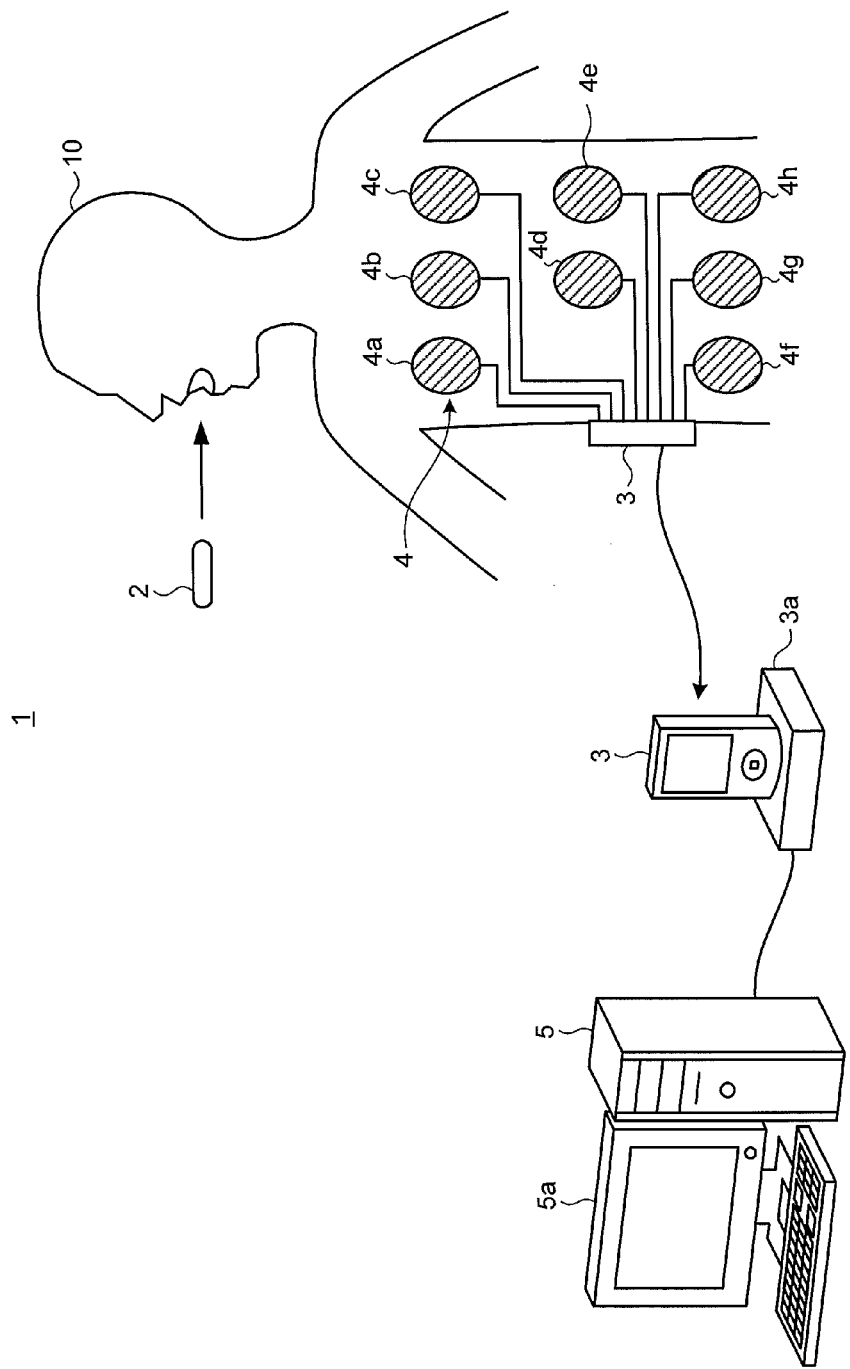
FIG. 1 is a schematic diagram illustrating a schematic configuration of a capsule endoscopic system including an image processing apparatus according to a first embodiment of the present invention.

FIG. 1 is a schematic diagram illustrating a schematic configuration of a capsule endoscopic system including an image processing apparatus according to a first embodiment of the present invention. A capsule endoscopic system 1 illustrated in FIG. 1 includes: a capsule endoscope 2, which generates image data by being introduced into a subject 10 and capturing an image of inside of the subject 10, and superimposes and transmits the image data on a wireless signal; a receiving device 3, which receives the wireless signal transmitted from the capsule endoscope 2 via a receiving antenna unit 4 that is attached to the subject 10; and an image processing apparatus 5, which acquires the image data from the receiving device 3 and performs predetermined image processing on the image data.

Figure 2:
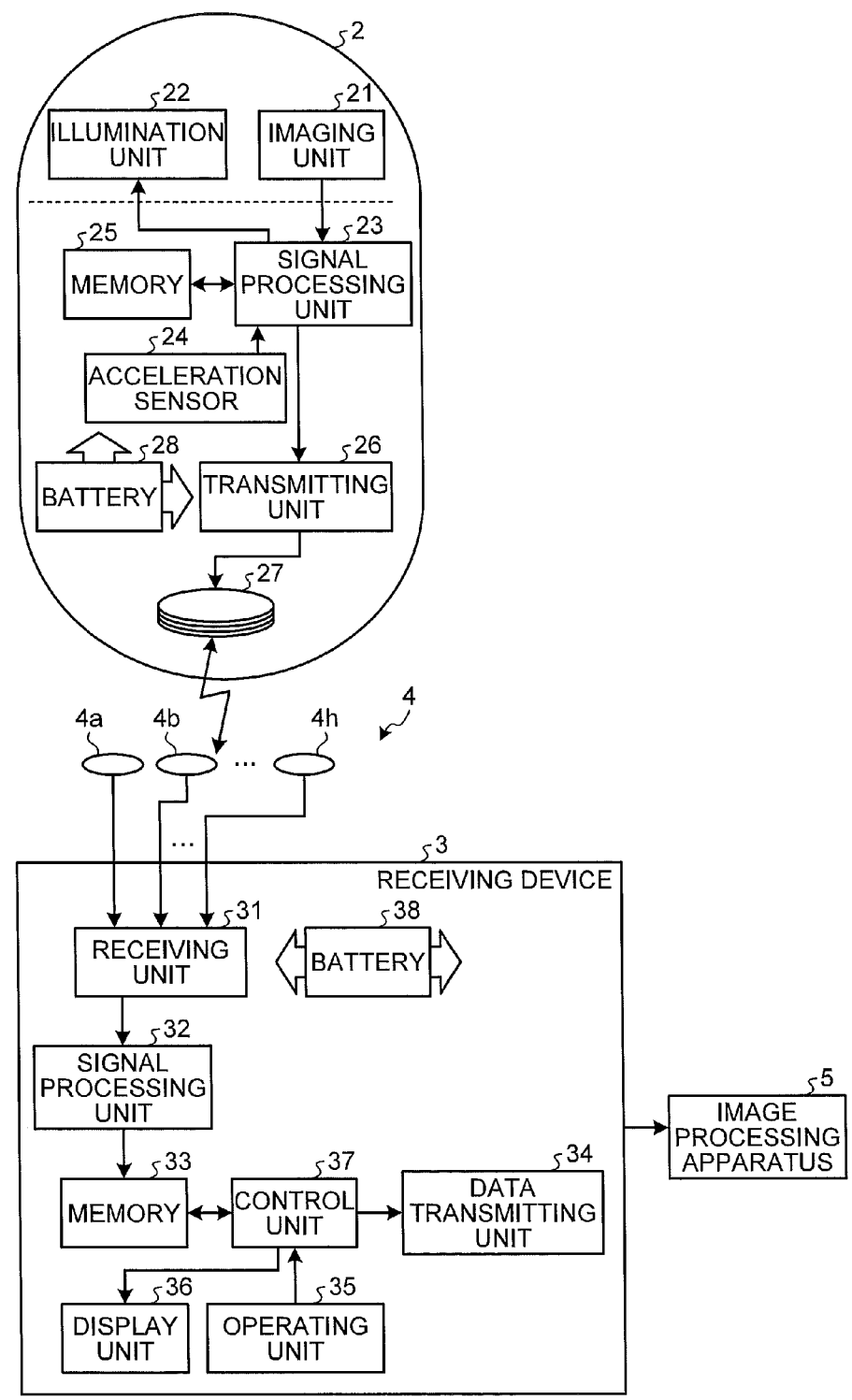
FIG. 2 is a diagram illustrating a schematic configuration of a capsule endoscope and a receiving device illustrated in FIG. 1.

FIG. 2 is a block diagram illustrating a schematic configuration of the capsule endoscope 2 and the receiving device 3.

The capsule endoscope 2 is a device, which has various built-in parts such as an imaging element in a capsule shaped casing of a size swallowable by the subject 10, and the capsule endoscope 2 includes: an imaging unit 21 that captures an image of the inside of the subject 10; an illumination unit 22 that illuminates the inside of the subject 10; a signal processing unit 23; an acceleration sensor 24 serving as means for detecting a posture of the capsule endoscope 2; a memory 25, a transmitting unit 26 and an antenna 27; and a battery 28.

The imaging unit 21 includes, for example: an imaging element such as a CCD or a CMOS, which generates and outputs an imaging signal representing the inside of the subject from an optical image formed on a light receiving surface; and an optical system such as an objective lens, which is arranged on a light receiving surface side of the imaging element.

The illumination unit 22 is realized by a light emitting diode (LED) or the like that emits light towards the inside of the subject when an image is captured.

The capsule endoscope 2 has a built-in circuit board (not illustrated) in which a driving circuit or the like that drives each of the imaging unit 21 and the illumination unit 22, and the imaging unit 21 and the illumination unit 22 are fixed on this circuit board in a state of directing a field thereof outward from one end portion of the capsule endoscope 2.

The signal processing unit 23 controls each unit in the capsule endoscope 2, performs A/D conversion on the imaging signal output from the imaging unit 21 to generate digital image data, and further performs predetermined signal processing on the digital image data.

The acceleration sensor 24 is arranged near a central portion of the casing of the capsule endoscope 2, for example, and detects accelerations in three axial directions given to the capsule endoscope 2 to output a detection signal. The detection signal output is stored in association with the image data generated at that time.

The memory 25 temporarily stores therein various operations executed by the signal processing unit 23 and the image data subjected to the signal processing in the signal processing unit 23.

The transmitting unit 26 and the antenna 27 superimpose, together with related information, the image data stored in the memory 25 on the wireless signal, and transmit the superimposed image data to outside.

The battery 28 supplies electric power to each unit in the capsule endoscope 2. The battery 28 includes a power source circuit that performs boosting or the like of electric power supplied from a primary battery or secondary battery such as a button battery.

After being swallowed by the subject 10, the capsule endoscope 2 sequentially captures images of living body sites (an esophagus, a stomach, a small intestine, a large intestine, and the like) at predetermined time intervals (for example, 0.5 second time intervals) while moving inside the digestive tract of the subject 10 by peristaltic movement or the like of organs. The image data and related information generated by this image capturing operation are sequentially transmitted wirelessly to the receiving device 3. The related information includes identification information (for example, a serial number) or the like allocated in order to individually identify the capsule endoscope 2.

Figure 8:
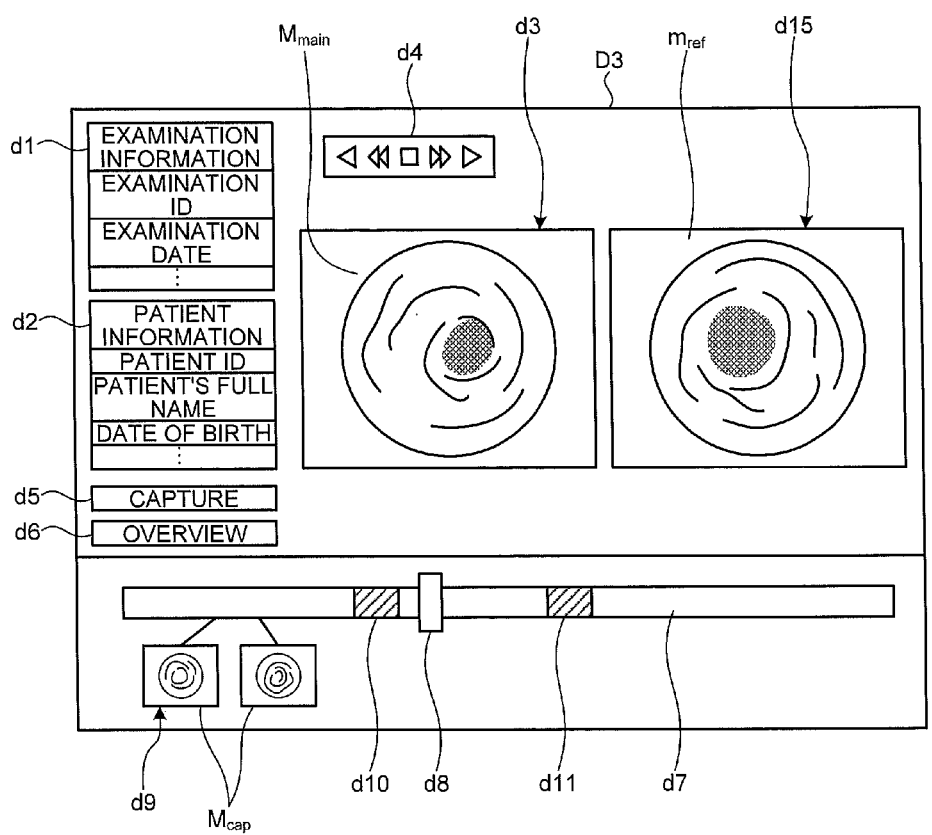
FIG. 8 is a schematic diagram illustrating a display example of an observation screen according to a modified example 1-5 of the first embodiment of the present invention.

The receiving device 3 receives the image data and related information wireless transmitted from the capsule endoscope 2, via the receiving antenna unit 4, which has a plurality of receiving antennas 4a to 4h (eight receiving antennas in FIG. 8). Each of the receiving antennas 4a to 4h is realized by using a loop antenna, for example, and the receiving antennas 4a to 4h are arranged at predetermined positions (for example, positions corresponding to respective organs in the subject 10 that are a passage route of the capsule endoscope 2) on a surface outside of a body of the subject 10.

As illustrated in FIG. 2, the receiving device 3 includes a receiving unit 31, a signal processing unit 32, a memory 33, a data transmitting unit 34, an operating unit 35, a display unit 36, a control unit 37, and a battery 38.

The receiving unit 31 receives the image data wirelessly transmitted from the capsule endoscope 2, via the receiving antennas 4a to 4h.

The signal processing unit 32 performs predetermined signal processing on the image data received by the receiving unit 31.

The memory 33 stores therein the image data subjected to the signal processing in the signal processing unit 32 and their related information.

The data transmitting unit 34 is an interface connectable with a USB or a communication line such as a wire LAN or a wireless LAN, and transmits, under control of the control unit 37, to the image processing apparatus 5, the image data and related information stored in the memory 33.

The operating unit 35 is used when a user inputs various setting information or the like.

The display unit 36 displays registration information (examination information, patient information, and the like) related to an examination and the various setting information or the like input by the user.

The control unit 37 controls operations of each of these units in the receiving device 3.

The battery 38 supplies electric power to each unit in the receiving device 3.

The receiving device 3 is attached to and carried by the subject 10 while image capturing is being performed by the capsule endoscope 2 (for example, while the capsule endoscope 2 is passing through the digestive tract after the capsule endoscope 2 is swallowed by the subject 10 and until the capsule endoscope 2 is excreted). During this period of time, the receiving device 3 adds, to the image data received via the receiving antenna unit 4, related information such as receiving intensity information and receiving time information in each of the receiving antennas 4a to 4h and stores these image data and related information in the memory 33. After completion of the image capturing by the capsule endoscope 2, the receiving device 3 is removed from the subject 10, connected to the image processing apparatus 5 next, and transfers the image data and related information stored in the memory 33 to the image processing apparatus 5. In FIG. 1, a cradle 3a is connected to a USB port of the image processing apparatus 5 and by setting the receiving device 3 in the cradle 3a, the receiving device 3 is connected to the image processing apparatus 5.

The image processing apparatus 5 is configured by using, for example, a work station including a display device 5a such as a CRT display or a liquid crystal display. The image processing apparatus 5 performs the predetermined image processing on the image of the inside of the subject 10 acquired via the receiving device 3, generates an observation screen of a predetermined format, and causes the display device 5a to display the observation screen.

Figure 3:
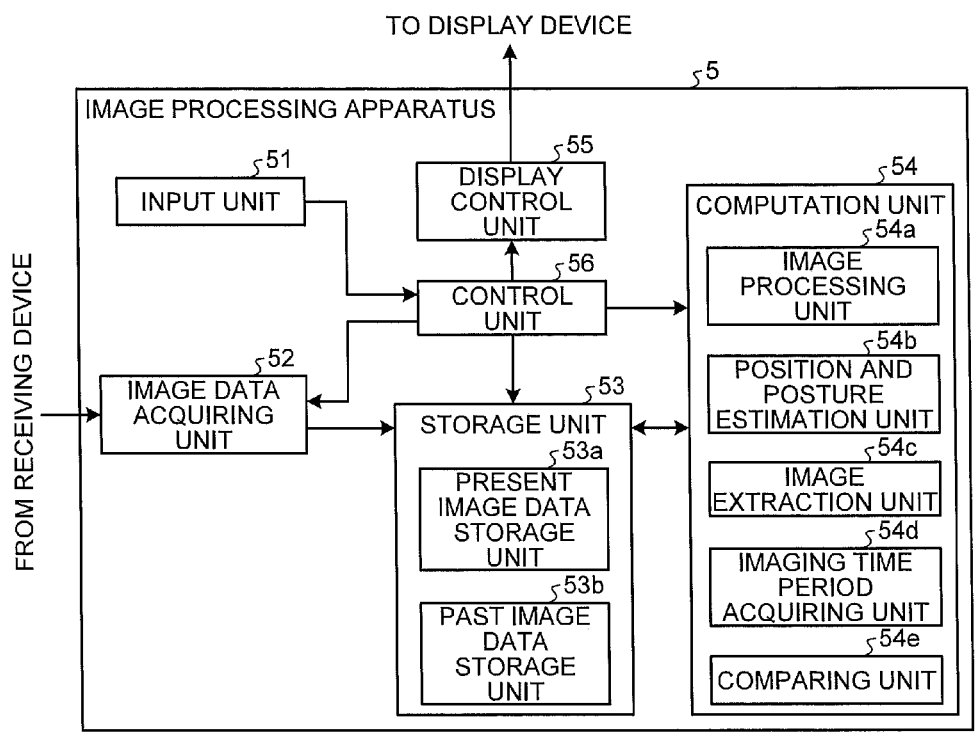
FIG. 3 is a block diagram illustrating a schematic configuration of the image processing apparatus illustrated in FIG. 1.

FIG. 3 is a block diagram illustrating a schematic configuration of the image processing apparatus 5. As illustrated in FIG. 3, the image processing apparatus 5 includes an input unit 51, an image data acquiring unit 52, a storage unit 53, a computation unit 54, a display control unit 55, and a control unit 56.

The input unit 51 is realized by an input device such as a key board and a mouse, a touch panel, or various switches. The input unit 51 receives input of information and an instruction according to the user's manipulation.

The image data acquiring unit 52 is an interface connectable with a USB or a communication line such as a wire LAN or wireless LAN, and includes a USB port, a LAN port, or the like. In the first embodiment, the image data acquiring unit 52 functions as a data acquiring unit that acquires the image data and related information from the receiving device 3 via an external device such as the cradle 3a connected to the USB port and via various communication lines.

The storage unit 53 is realized by a semiconductor memory such as a flash memory, a RAM, or a ROM, or a recording medium such as an HDD, an MO, a CD-R, or a DVD-R, and a read and write device or the like that performs reading and writing of information from and to the recording medium. The storage unit 53 stores therein programs and various information for causing the image processing apparatus 5 to operate and execute various functions, and image data or the like acquired by a capsule endoscopic examination. In more detail, the storage unit 53 includes: a present image data storage unit 53a that stores therein, together with the related information, the image data generated in a present examination and acquired from the receiving device 3; and a past image data storage unit 53b that stores therein image data acquired in a past examination and subjected to later described image processing.

The computation unit 54 is realized by hardware such as a CPU, and by reading a predetermined program stored in the storage unit 53, performs the predetermined image processing on the image data acquired by the image data acquiring unit 52, generates the image data for displaying the images in the predetermined format, and executes predetermined processing for generating the observation screen.

In more detail, the computation unit 54 includes: an image processing unit 54a; a position and posture estimation unit 54b; an image extraction unit 54c; an imaging time period acquiring unit 54d; and a comparing unit 54e.

The image processing unit 54a generates image data for display by performing image processing (hereinafter, referred to as "image processing for display") such as a white balance process, demosaicing, color conversion, intensity conversion (gamma conversion or the like), smoothing (noise removal or the like), or sharpening (edge enhancement or the like), and performs image processing such as an average color calculation process, a lesion detection process, a red color detection process, an organ detection process, or a predetermined feature detection process. Information such as an average color, a lesion detection result, a red color detection result, an organ detection result, or a predetermined feature detection result (hereinafter, referred to as "feature detection information") is associated with the image data and stored in the storage unit 53 with the image data.

The position and posture estimation unit 54b estimates, based on the receiving intensity information and receiving time information acquired as the related information of the image data, a position of the capsule endoscope 2 inside the subject 10 at an imaging time of an image. Further, any of various known methods may be used as a method of estimating the position. Further, the position and posture estimation unit 54b estimates, based on the detection signal of the acceleration acquired as related information of the image data, a posture of the capsule endoscope 2 with respect to a travelling direction of the capsule endoscope 2. A result of the estimation of the position and posture is associated with the image data and stored in the storage unit 53.

The image extraction unit 54c extracts, based on the feature detection information associated with the image data stored in the present image data storage unit 53a, a plurality of images (hereinafter, referred to as "feature images") representing a predetermined feature from an image data group (hereinafter, referred to as "present image group") corresponding to the image data. Further, the image extraction unit 54c extracts, based on the feature detection result associated with the image data stored in the past image data storage unit 53b, feature images corresponding to the feature images extracted from the present image group, from an image group (hereinafter, referred to as "past image group") corresponding to the image data.

Because the capsule endoscope 2 moves inside the digestive tract by the peristaltic movement of the digestive tract of the subject 10, controlling the position and posture of the capsule endoscope 2 is difficult, and images of the same composition are rarely acquired between a present examination and a past examination. Further, since the small intestine is constantly making the peristaltic movement and has no determined shape, identification of the position of the capsule endoscope 2 is also difficult.

However, even in the digestive tract, for a site identifiable by color such as an entrance of a stomach, for a site having a characteristic shape such as a pylorus, a duodenal bulb, a Vater's papilla, a Peyer patch, or a Bauhin's valve, for a ulcer specific to the subject, or for a location where a clip is placed, for example, the site is comparatively easy to be identified even if the composition is different. Even though the small intestine makes the peristaltic movement, a portion that is at an upper right abdominal region, for example, will not move to a bottom left abdominal region and should remain within a positional change of a certain range, and thus a characteristic site like that described above should be generally present at positions close to each other between a present examination and a past examination. Accordingly, correspondence between different examinations is possible for images in which the site exemplified above is photographed. Therefore, in the first embodiment, the image in which the above described site is photographed is extracted as a landmark. Specifically, images exemplified below are extracted.

(1) Image of Location at which Image Capturing Started

This is a first image of an image group.

(2) an Image of Entrance of Stomach (Boundary from Esophagus)

A color of an esophagus on average is pinkish, while a color of a stomach on average is reddish, and thus an image of an entrance of the stomach is identifiable from, for example, a change in average color of the image.

(3) Pylorus Image

A pylorus is a portion of a stomach that connects to a duodenum. An average color of an image of the stomach is reddish and an average color of an image of the duodenum is yellowish, and thus an image in which the pylorus is photographed is identifiable from, for example, a change in average color of the image.

(4) Duodenal Bulb Image

A duodenal bulb is an entrance of the duodenum and has a shape spherically swelled. The duodenal bulb photographed in an image is identifiable by, for example, its shape.

(5) Vater's Papilla Image

A Vater's papilla is a portion that opens, at where a major bile duct joins a main pancreatic duct. The Vater's papilla photographed in an image is identifiable by, for example, its shape.

(6) Peyer Patch Image

A Peyer patch is a region in which regions having underdeveloped villi are scattered in a patchwork manner; and of a small intestine (a duodenum, a jejunum, and an ileum), the jejunum and ileum are identifiable image-wise by presence or absence of the Peyer patch. An image in which the Peyer patch is photographed is identifiable by, for example, its shape or texture.

(7) Bauhin's Valve Image

A Bauhin's valve is a valve at a boundary between the ileum and a cecum, and indicates an end of the ileum. An image in which the Bauhin's valve is photographed is identifiable by, for example, its shape.

(8) Ulcer Image

An image in which an ulcer is photographed is extractable by, for example, a red color detection process.

(9) Image of Location where Clip is Placed (Clip Image)

An image in which a clip is photographed is extractable, for example, by a matching process having a particular clip shape as a template.

An image to be extracted is not limited to the above described (1) to (9), and, a parameter indicating an abnormal site (a region where no villi are present, a region where villi are raised, or a region where a form of the villi has changed (been enlarged or the like)) may be calculated and an image having the parameter within a predetermined range may be extracted as the feature image.

The imaging time period acquiring unit 54d acquires an interval (imaging time period) between imaging times among a plurality of feature images extracted from the present image group. Further, the imaging time period acquiring unit 54d acquires, similarly with respect to the past image group, an interval (imaging time period) between imaging times of the extracted feature images.

The comparing unit 54e compares the imaging time period acquired from the present image group and the imaging time period acquired from the past image group by the imaging time period acquiring unit 54d, determines whether or not a difference between them is equal to or greater than a predetermined reference value, and adds a predetermined flag to the feature images extracted from the present image group and the images therebetween if the difference between them is equal to or greater than the predetermined reference value.

The display control unit 55 performs control of causing the display device 5a to display the observation screen including the present images in the predetermined format. When this is done, the display control unit 55 performs, based on a result of the comparison by the comparing unit 54e, the display of the images added with the above described predetermined flag in a format of attracting the user's attention.

The control unit 56 is realized by hardware such as a CPU, and by reading various programs stored in the storage unit 53, performs, based on a signal input via the input unit 51 and the image data or the like acquired by the image data acquiring unit 52, transfer or the like of instructions and data to each unit forming the image processing apparatus 5, and comprehensively controls operations of the whole image processing apparatus 5.

Figure 4:
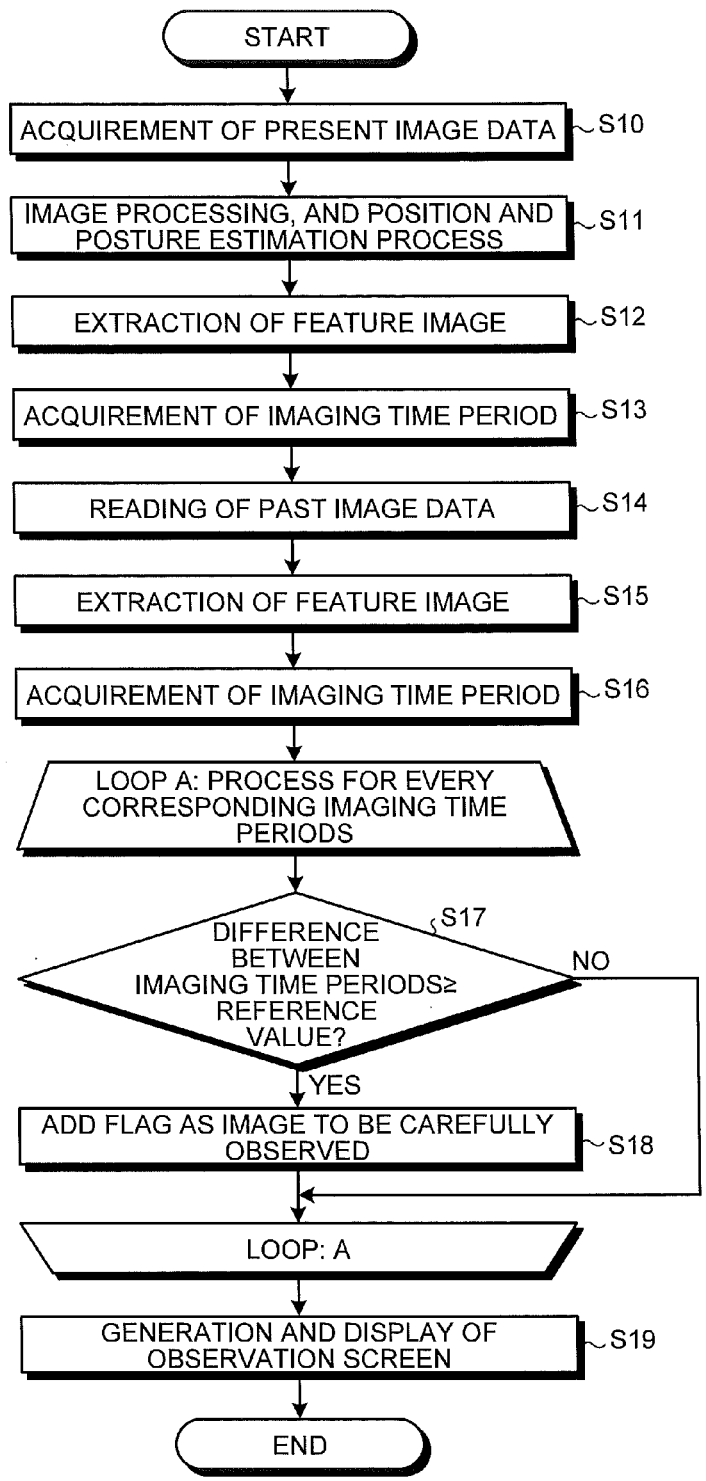
FIG. 4 is a flow chart illustrating operations of the image processing apparatus illustrated in FIG. 3.
Figure 5:
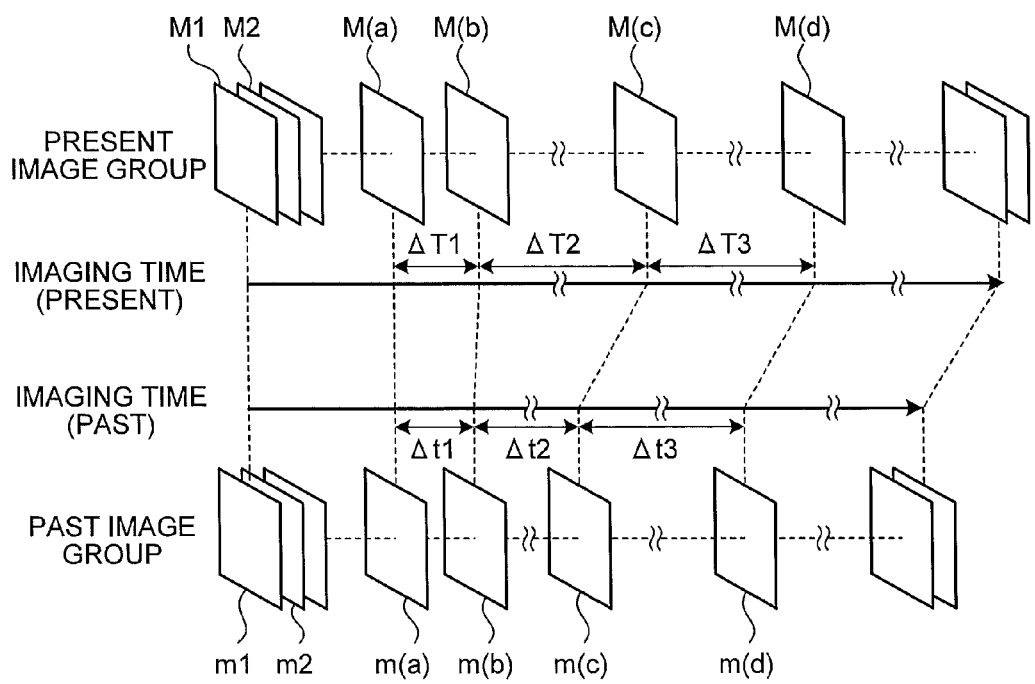
FIG. 5 is a schematic diagram illustrating the operations of the image processing apparatus illustrated in FIG. 3.

Next, operations of the image processing apparatus 5 will be described. FIG. 4 is a flow chart illustrating the operations of the image processing apparatus 5. Further, FIG. 5 is a schematic diagram illustrating the operations of the image processing apparatus 5.

First, at step S10, the image processing apparatus 5 acquires from the receiving device 3 an image data (a present image data) generated by a capsule endoscopic examination presently performed, and temporarily stores the image data in the storage unit 53.

At subsequent step S11, the image processing unit 54a fetches the present image data from the storage unit 53, performs image processing for display on the present image data, and performs image processing such as an average color calculation process, a lesion detection process, a red color detection process, an organ detection process, a predetermined feature detection process, or the like to generate feature detection information. Further, the position and posture estimation unit 54b estimates, based on related information of the image data (receiving intensity information, receiving time information, and a detection signal of an acceleration), a position and a posture of the capsule endoscope 2 at an imaging time of each image.

At step S12, the image extraction unit 54c extracts from the present image group M1, M2, . . . , two or more of the feature images exemplified in the above described (1) to (9). In the first embodiment, as exemplified in FIG. 5, a pylorus image M(a), a clip image M(b), a Vater's papilla image M(c), and a Bauhin's valve image M(d) are assumed to be extracted.

At step S13, the imaging time period acquiring unit 54d acquires an imaging time period between the feature images extracted from the present image group. Specifically, as illustrated in FIG. 5, an imaging time period ΔT1, which is an interval between the pylorus image M(a) and the clip image M(b), an imaging time period ΔT2, which is an interval between the clip image M(b) and the Vater's papilla image M(c), and an imaging time period ΔT3, which is an interval between the Vater's papilla image M(c) and the Bauhin's valve image M(d), are calculated.

At subsequent step S14, the computation unit 54 reads out, from the storage unit 53, image data acquired in a past examination. When this is done, if a predetermined feature detection process or the like has not been performed on a past image group corresponding to past image data, the image processing unit 54a may execute that process at this timing to generate feature detection information.

At subsequent step S15, the image extraction unit 54c extracts, from the past image group, based on the feature detection information of each image, feature images corresponding to the feature images extracted from the present image group. Specifically, as illustrated in FIG. 5, from the past image group m1, m2, . . . , a pylorus image m(a), a clip image m(b), a Vater's papilla image m(c), and a Bauhin's valve image m(d) are extracted. If a feature image corresponding to the feature image extracted from the present image group M1, M2, . . . is not detectable from the past image group, that may not be detected.

At step S16, the imaging time period acquiring unit 54d acquires an imaging time period between the feature images extracted from the past image group. In FIG. 5, an imaging time period Δt1 between the pylorus image m(a) and the clip image m(b), an imaging time period Δt2 between the clip image m(b) and the Vater's papilla image m(c), and an imaging time period Δt3 between the Vater's papilla image m(c) and the Bauhin's valve image m(d) are calculated.

Subsequently, the comparing unit 54e performs processing of steps S17 and S18 for respective imaging time periods corresponding to each other between the present image group and the past image group. Specifically, in FIG. 5, the imaging time periods ΔT and Δt1 between the pylorus images M(a) and m(a) and the clip images M(b) and m(b), the imaging time periods ΔT2 and Δt2 between the clip images M(b) and m(b) and the Vater's papilla images M(c) and m(c), and the imaging time periods ΔT3 and Δt3 between the Vater's papilla images M(c) and m(c) and the Bauhin's valve images M(d) and m(d) are respectively the corresponding imaging time periods.

At step S17, the comparing unit 54e respectively calculates differences between the imaging time periods acquired from the present image group and the imaging time periods acquired from the past image group and determines whether or not the differences are equal to or greater than predetermined reference values. The reference value may be defined to be of a relative value, such as, for example, "30% of the imaging time period acquired from the past image group".

If the difference between the imaging time periods is equal to or greater than the predetermined reference value (step S17: Yes), the comparing unit 54e adds a careful observation flag, which indicates that an image is an image to be carefully observed, to a series of images captured during that imaging time period in the present examination (step S18). For example, in FIG. 5, since the present imaging time period ΔT2 is greatly longer than the past imaging time period Δt2, the careful observation flag is added to images in the present image group from the clip image M(b) to the Vater's papilla image M(c).

The reason for adding the careful observation flag is that it is considered that there is a possibility that a new factor (a tumor, a change in shape, stagnation of a residue, or the like) that inhibits movement of the capsule endoscope 2 at a corresponding site in the subject 10 has been newly generated when there is a wide increase in imaging time period between landmarks (the clip image M(b) and m(b) and the Vater's papilla image M(c) and m(c)) common between the present image group and the past image group.

On the contrary, if the difference between the imaging time periods is less than the predetermined reference value (step S17: No), the processing proceeds directly to the next step. For example, in FIG. 5, between the imaging time periods ΔT1 and Δt1, and between the imaging time periods ΔT3 and Δt3, large differences are not found, and thus a flag is not particularly added to images from the pylorus image M(a) to the clip image M(b) and the Vater's papilla image M(c) to the Bauhin's valve image M(d).

At step S19, the display control unit 55 generates an observation screen including the present image group and causes the display device 5a to display the observation screen. When this is done, the display control unit 55 performs control to cause the images added with the careful observation flag to be displayed in a format different from that for other images, in order to attract attention of a medical worker and make the medical worker to make observation intensively.

Figure 6:
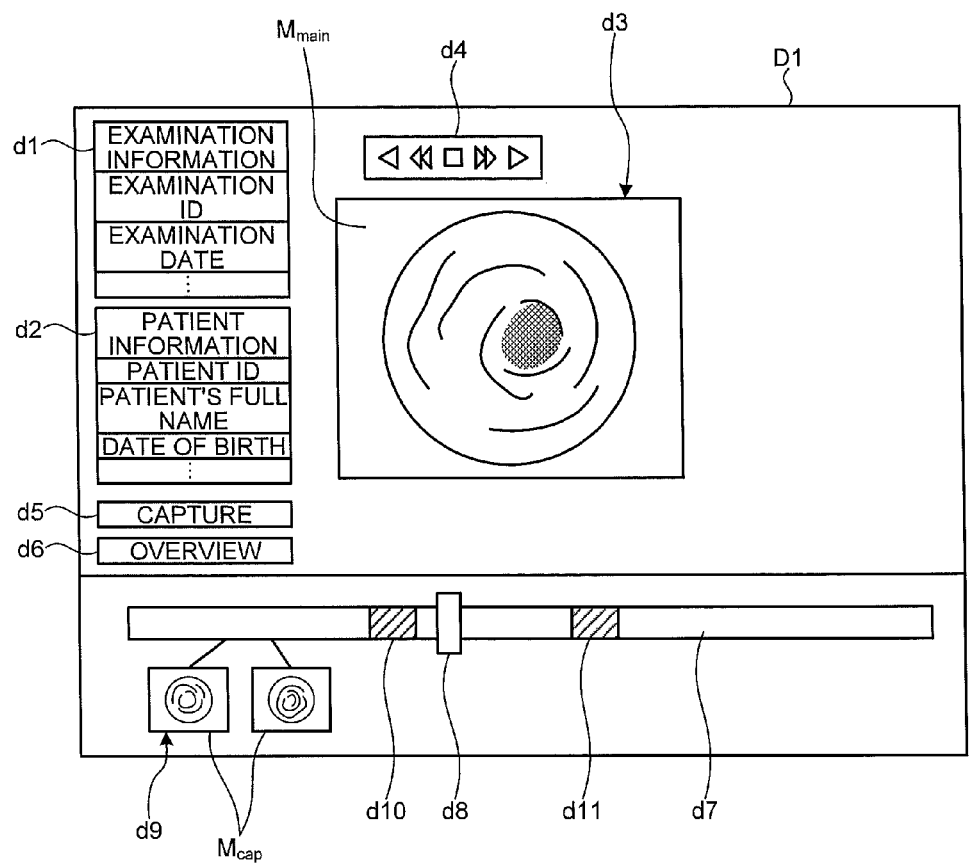
FIG. 6 is a schematic diagram illustrating an example of an observation screen displayed on a display device illustrated in FIG. 1.

FIG. 6 is a schematic diagram illustrating an example of an observation screen displayed on the display device 5a. An observation screen D1 illustrated in FIG. 6 includes: an examination information display column d1 where examination information such as an examination ID and an examination date is displayed; a patient information display column d2 where patient information such as a patient ID, a patient's full name, and a date of birth is displayed; a main display area d2 where present images $M_{main}$ acquired in the present examination are sequentially displayed as a pseudo moving image; a playback operating button group d4 used when a user manipulates playback operations of the present image group sequentially displayed in the main display area d3; a capture button d5 that is used when the user inputs an instruction to capture an image that is being displayed in the main display area d3; and an overview button d6 that is used when the user inputs an instruction to switch over a display format of the present image group displayed on the observation screen D1 from a pseudo moving image format to a still image list display format.

Below the main display area d3, a time bar d7 and a slider d8 that represent an imaging time of the present image $M_{main}$ being displayed in the main display area d3, and a captured image display area d9, in which a list of the captured images is displayed as thumbnails, are provided. In order to illustrate an imaging time of each image $M_{cap}$ captured, a line joining each image $M_{cap}$ and a position on the time bar d7 corresponding to the imaging time may be displayed.

On the time bar d7, areas d10 and d11 corresponding to the images added with the careful observation flag are displayed to be distinguishable from other areas. Specifically, these areas d10 and d11 are displayed in a different color from that of the other areas. FIG. 6 illustrates a difference in color by presence or absence of hatching. Or, the areas d10 and d11 may be displayed to be blinking. The user is able to grasp images to be carefully observed from the present image group by referring to the time bar d7 as described.

In the observation screen D1 as described, when a signal instructing start of playback of the present image group is input to the image processing apparatus 5 by a pointer operation with respect to the playback operating button group d4 using the input unit 51 (mouse or the like), a series of present images are sequentially switched over at a predetermined display frame rate in the main display area d3 for display.

The display control unit 55 decreases a display frame rate in the main display area d3 and increases a display time period per image, when a turn to display the images added with the careful observation flag comes around. Thereby, the user is able to pay attention to the images added with the careful observation flag and make the observation intensively.

When the turn to display the images added with the observation flag comes around, the display control unit 55 may pause the playback of images or display on the observation screen D1 a message indicating that an image is the image to be carefully observed, in order to attract the user's attention.

Or, the display control unit 55 may increase a display speed by performing decimated display at a predetermined rate on images not added with the careful observation flag and when the turn to display the images added with the careful observation flag comes around, may stop the decimated image and sequentially display all of the images. In this case, the user is able to intensively observe throughout the images added with the careful observation flag and observe the other images simply, and thus to improve an observation efficiency.

Further, the display control unit 55 may display the images added with the careful observation flag as thumbnails in the captured image display area d9 side by side. In that case, the user is able to grasp the whole picture of the images to be carefully observed at first sight.

The operations of the image processing apparatus 5 are ended after such display of the observation screen D1.

As described above, in the first embodiment, between the present image group and the past image group, the images in the region greatly different in the imaging time periods between the feature images are emphasized, or displayed in a format distinguishable by the user. Accordingly, the user is able to make observation intensively and perform diagnosis on an image of a site in a subject having a possibility of having a certain change caused between the past examination and the present examination. Therefore, it becomes possible to increase a discovery efficiency of an abnormal site and to shorten an observation time period as a whole, and thus to improve an observation efficiency.

Modified Example 1-1

Next, a modified example 1-1 of the first embodiment of the present invention will be described.

In the first embodiment, as a quantity corresponding to a time period between the imaging times of the plurality of feature images extracted respectively from the present image group and the past image group, the imaging time period is acquired (see step S13 and S16). However, instead of the imaging time period, the number the series of images captured between a certain feature image and another feature image may be acquired. Since image capturing is performed at a constant imaging frame rate normally in the capsule endoscope 2, the imaging time period and the number of images are corresponding quantities. In this case, at step S17 of FIG. 4, whether or not a difference between the number of images of an interval acquired from the present image group and the number of images of a corresponding interval acquired from the past image group is equal to or greater than a predetermined value is determined.

Modified Example 1-2

Next, a modified example 1-2 of the first embodiment of the present invention will be described.

When the images added with the careful observation flag are displayed on the observation screen D1, the display may be performed after performing further predetermined image processing on these images. For example, on the images added with the careful observation flag, an image analysis process of extracting a predetermined lesion region may be performed, and when these images are displayed in the main display area d3, a result of that analysis may be displayed therewith.

In addition, the careful observation flag may be used as a parameter of various aiding functions for generating and displaying the observation screen.

Modified Example 1-3

Next, a modified example 1-3 of the first embodiment of the present invention will be described.

In the observation screen illustrated in FIG. 6, although the time bar d7 representing a time scale is displayed, instead of the time bar d7, an average color bar, of which average colors of respective images included in the present image group are lined along a time axis, may be displayed. In this case, a user is able to check changes in types of organs corresponding to the average colors of the images by visually observing the average color bar. Further, in this case, an area on the average color bar corresponding to the images added with the careful observation flag preferably attracts the user's attention by blinking or the like.

Modified Example 1-4

Next, a modified example 1-4 of the first embodiment of the present invention will be described.

Figure 7:
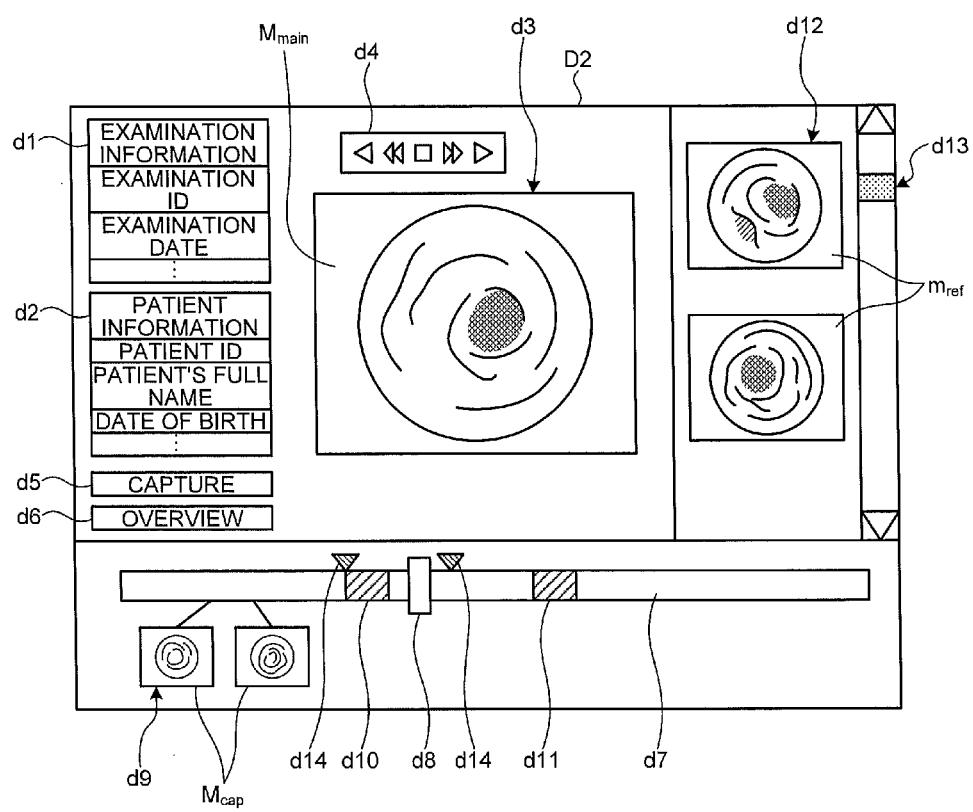
FIG. 7 is a schematic diagram illustrating a display example of an observation screen according to a modified example 1-4 of the first embodiment of the present invention.

FIG. 7 is a schematic diagram illustrating a display example of an observation screen in the modified example 1-4. On the observation screen D1 illustrated in FIG. 6, only the present image group is displayed, but in addition to the present image group, the past image group may be displayed on the same screen.

On an observation screen D2 illustrated in FIG. 7, in addition to the observation screen D1, a past image display area d12, in which a past image $m_{ref}$ as a reference image is displayed, is provided further. In this past image display area d12, a scroll bar d13 for scrolling the past image $m_{ref}$ is provided. At a position on the time bar d7 corresponding to an imaging time of the past image $m_{ref}$ being displayed in the past image display area d12, a marker d14 may be displayed further.

The past image $m_{ref}$ displayed in the past image display area d12 may be an image captured during observation of the past image group, may be an image of the past image group corresponding to the image added with the careful observation flag in the present image group (that is, of those having the imaging time periods compared at step S17), or may be an image determined to be abnormal in an observation performed in the past and added with a predetermined label.

Modified Example 1-5

Next, a modified example 1-5 of the first embodiment of the present invention will be described.

FIG. 8 is a schematic diagram illustrating a display example of an observation screen in the modified example 1-5. In an observation screen D3 illustrated in FIG. 8, in addition to the observation screen D1 illustrated in FIG. 6, a past image display area d15, in which a past image $m_{ref}$ corresponding to the present image $M_{main}$ being displayed in the main display area d3 is displayed, is further provided. The present image $M_{main}$ being displayed and the corresponding past image $m_{ref}$ are, for example, able to be estimated by performing proportional division on an interval (see FIG. 5) between imaging times of feature images corresponding between the present image group and the past image group. The past image display area d15 as described may be always displayed on the screen or displayed only while the image added with the careful observation flag is being displayed in the main display area d3. Or, display/non-display may be switched over by a user's manipulation.

Modified Example 1-6

Next, a modified example 1-6 of the first embodiment of the present invention will be described.

Figure 9:
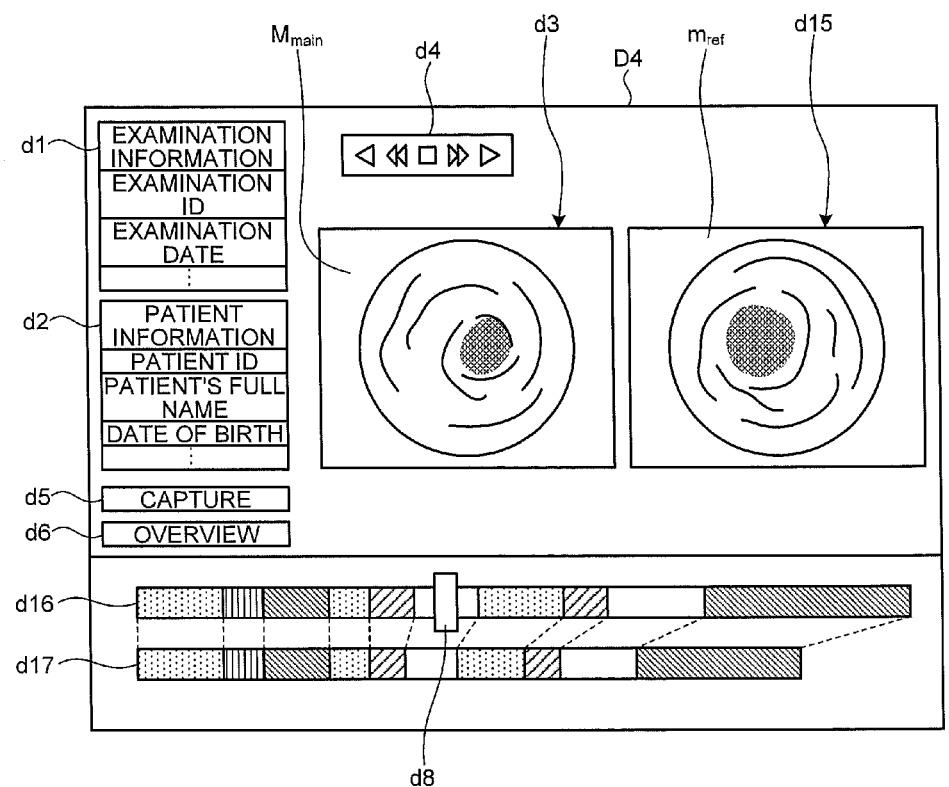
FIG. 9 is a schematic diagram illustrating a display example of an observation screen according to a modified example 1-6 of the first embodiment of the present invention.

FIG. 9 is a schematic diagram illustrating a display example of an observation screen in the modified example 1-6. On an observation screen D4 illustrated in FIG. 9, instead of the time bar d7 and the captured image display area d9 illustrated in FIG. 6, an average color bar d16 generated from the present image group and an average color bar d17 generated from the past image group are provided. The average color bar d16 and average color bar d17 are joined by lines linking imaging times of mutually corresponding feature images. FIG. 9 illustrates a difference in color by presence or absence of hatching.

As described, by comparably displaying the two average color bars d16 and d17, a medical worker is able to grasp a site where a change has occurred in the subject 10 between a past examination and a present examination.

Modified Example 1-7

Next, a modified example 1-7 of the first embodiment of the present invention will be described.

Figure 10:
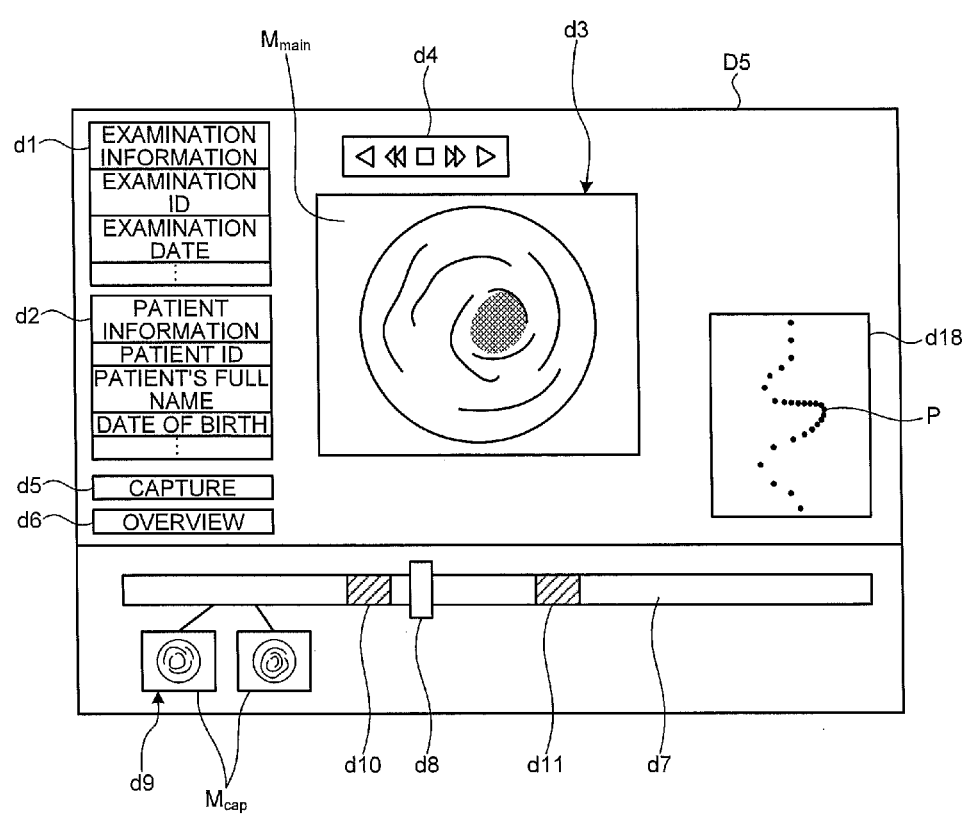
FIG. 10 is a schematic diagram illustrating a display example of an observation screen according to a modified example 1-7 of the first embodiment of the present invention.

FIG. 10 is a schematic diagram illustrating a display example of an observation screen in the modified example 1-7. On an observation screen D5 illustrated in FIG. 10, in addition to the observation screen D1 illustrated in FIG. 6, a track display area d18 is provided, in which a track of the capsule endoscope 2 in the subject 10 is displayed. In the track display area d18, a position of the capsule endoscope 2 at an imaging time of each image estimated by the position and posture estimation unit 54b is indicated by a dotted mark "P".

For the track display area d18 as described, in this modified example 1-7, the mark "P" indicating the positions of the images added with the careful observation flag is more densely displayed than the mark "P" indicating positions of the other images. Thereby, a medical worker is able to more accurately grasp a position in the subject 10 of an image to be intensively observed.

Modified Example 1-8

Next, a modified example 1-8 of the first embodiment of the present invention will be described.

Figure 11:
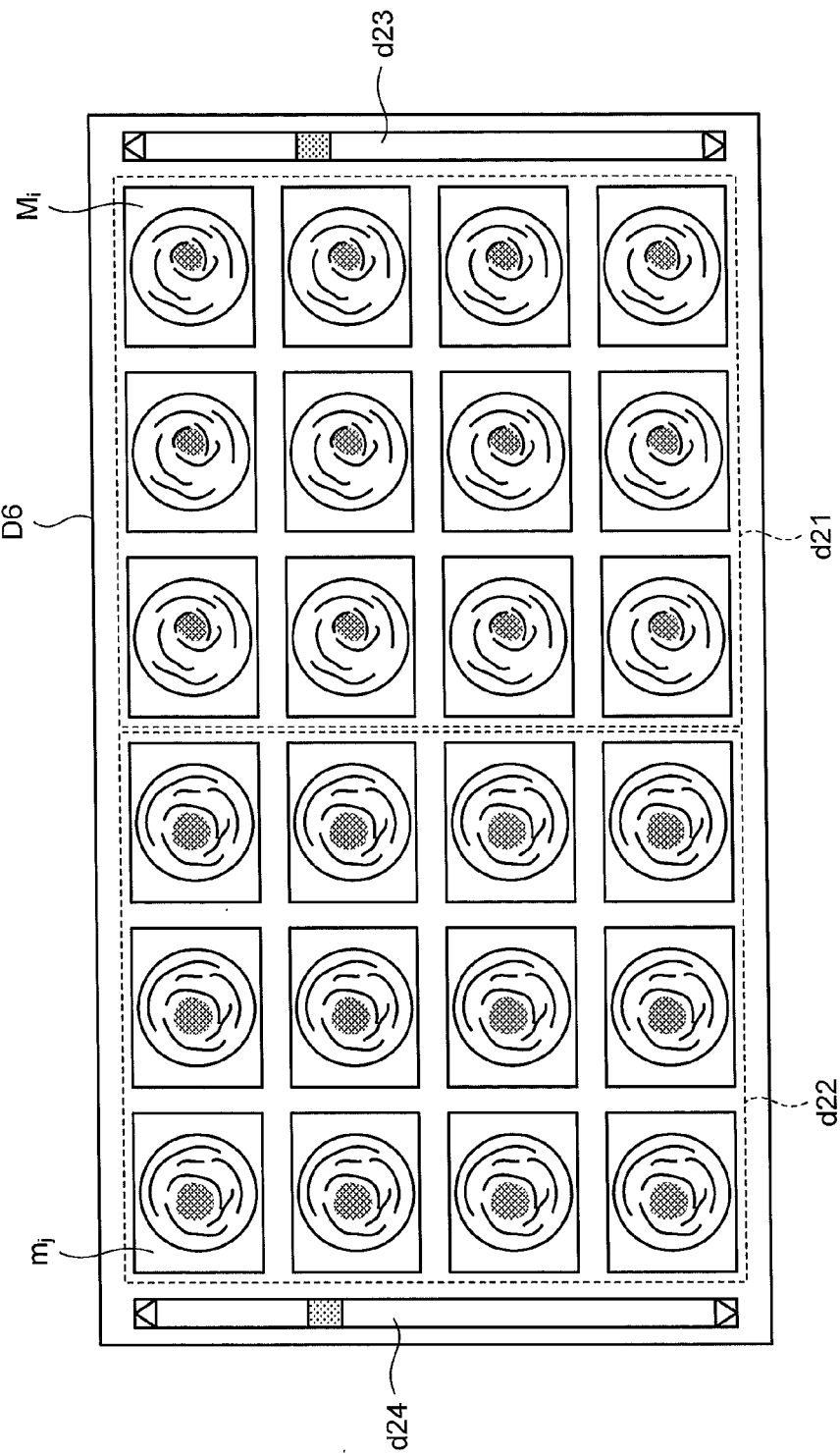
FIG. 11 is a schematic diagram illustrating a display example of an observation screen according to a modified example 1-8 of the first embodiment of the present invention.

FIG. 11 is a schematic diagram illustrating a display example of an observation screen in the modified example 1-8. On an observation screen D6 illustrated in FIG. 11, a present image list display area d21 and a past image list display area d22 are provided. The present image list display area d21 is an area, in which a list of a plurality of present images $M_i$ added with the careful observation flag are displayed as still images. Further, the past image list display area d22 is an area, in which a list of a plurality of past images $m_j$ corresponding to the present images $M_i$ displayed in the present image list display area d21 are displayed as still images.

In the present image list display area d21, a scroll bar d23 for scrolling the area is provided. Further, in the past image list display area d22, a scroll bar d24 for scrolling that area is provided. These scroll bars d23 and d24 may be set to operate in conjunction with each other or set to operate independently from each other. Transition to this observation screen D6 is possible by a pointer operation on the overview button d6 from the observation screen D1 illustrated in FIG. 6, for example.

A user is able to grasp a progress of symptoms or the like by comparing the present images $M_i$ to be intensively observed and the past images $m_j$ corresponding thereto by the observation screen D6 as described.

Figure 12:
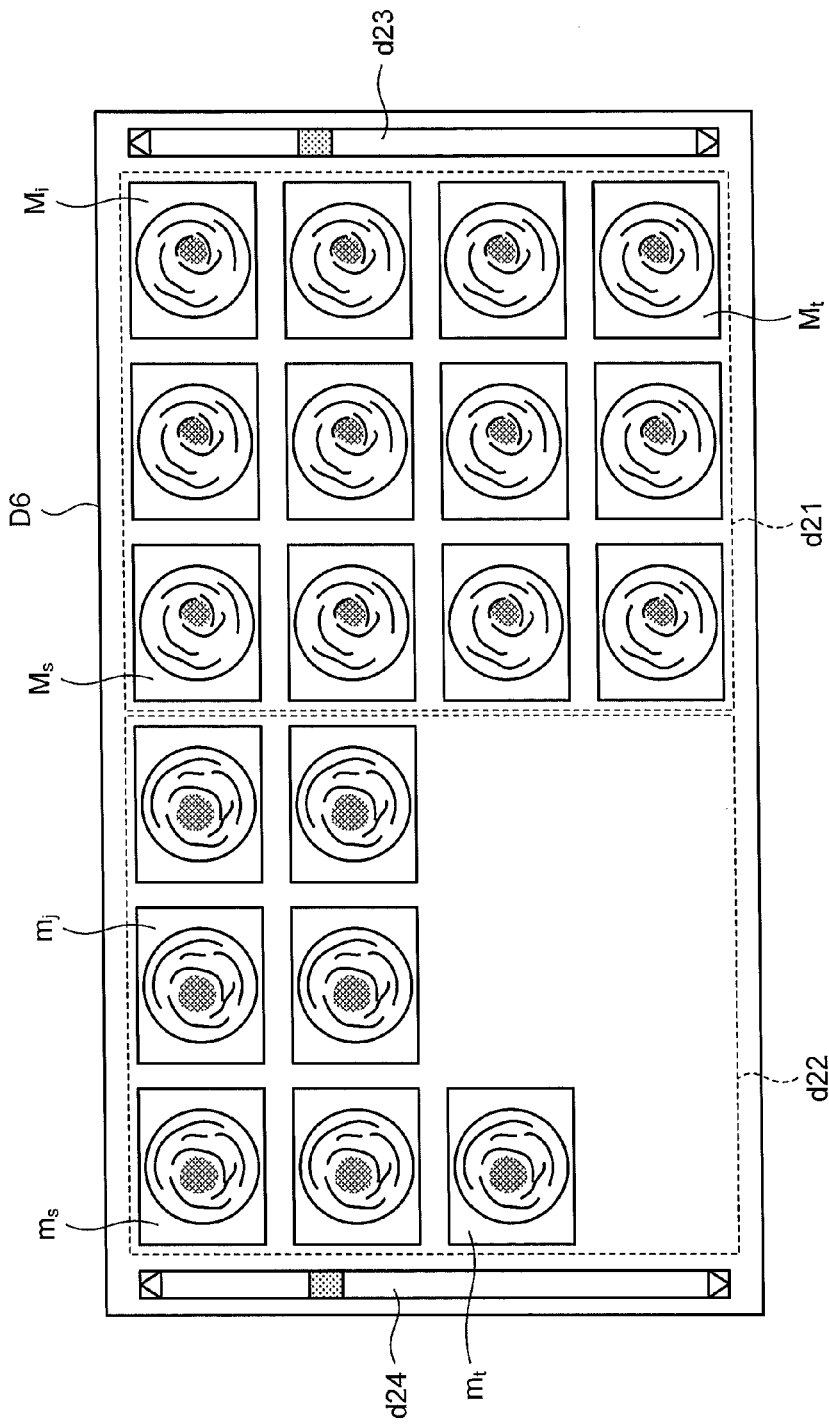
FIG. 12 is a schematic diagram illustrating another display example of the observation screen according to the modified example 1-8 of the first embodiment of the present invention.

Even when images are captured in a present examination and a past examination for a same site in the subject 10, the number of images captured, like between the clip images M(b) and m(b) and the Vater's papilla image M(c) and m(c), may differ from each other. In such a case, as illustrated in FIG. 12, in the past image list display area d22, only past images $m_s$ to $m_t$ of a range corresponding to present images $M_1$ to $M_t$ displayed in the present image list display area d21 may be displayed, with feature images $M_s$ and $m_s$ and feature images $M_t$ and $m_t$ corresponding to each other between the present image group and the past image group being landmarks.

Second Embodiment

Next, a second embodiment of the present invention will be described.

Figure 13:
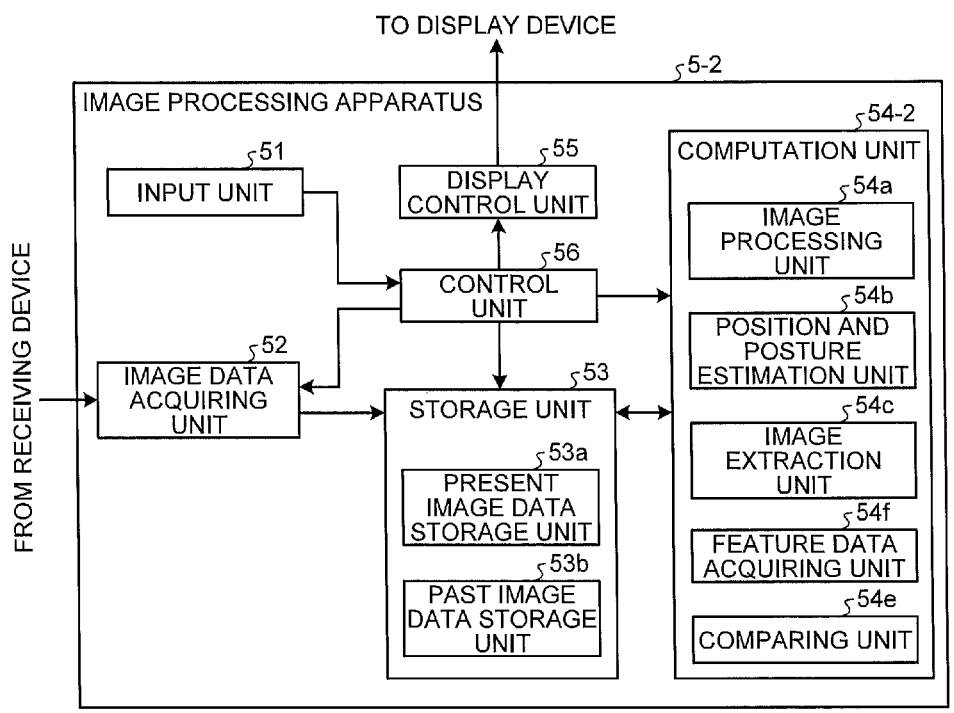
FIG. 13 is a block diagram illustrating a schematic configuration of an image processing apparatus according to a second embodiment of the present invention.

FIG. 13 is a block diagram illustrating a schematic configuration of an image processing apparatus according to the second embodiment of the present invention. As illustrated in FIG. 13, a image processing apparatus 5-2 according to the second embodiment includes a computation unit 54-2 having a feature data acquiring unit 54f instead of the imaging time period acquiring unit 54d in the image processing apparatus 5 illustrated in FIG. 3. A configuration of the computation unit 54-2 and the whole image processing apparatus 5-2 other than the feature data acquiring unit 54f is similar to that illustrated in FIG. 3.

The feature data acquiring unit 54f acquires feature data characterizing movement of the capsule endoscope 2, among a plurality of feature images extracted respectively from the present image group and the past image group by the image extraction unit 54c. Hereinafter, the feature data acquired from the present image group is referred to as "present feature data" and the feature data acquired from the past image group is referred to as "past feature data".

Further, in the second embodiment, the comparing unit 54e compares between the present feature data and the past feature data acquired by the feature data acquiring unit 54f and determines whether or not a difference between them is equal to or greater than a predetermined reference value.

The feature data characterizing the movement of the capsule endoscope 2, as exemplified below, may be a parameter indicating a change in feature data of an image calculated by the image processing unit 54a, a parameter indicating a movement or a change in position of the capsule endoscope 2 calculated by the position and posture estimation unit 54b, or the like. Hereinafter, a first feature image is an arbitrary feature image extracted from the present image group (or past image group), and a second feature image is a feature image extracted next to the first feature image in the order of imaging time.

(1) Statistic of Average Color of Image

An average color of each image between the first feature image and the second feature image is calculated and a statistic (an average value, a mode value, or the like) of a parameter indicating the average color is set as the feature data. If a difference between a statistic calculated as the present feature data and a statistic calculated as the past feature data is large, it can be said that there is a possibility that a certain new change has occurred between the past examination and the present examination at a site in the subject 10 corresponding to these images.

(2) Parameter Indicating Change in Color

An average color of each image between the first feature image and the second feature image is calculated and a parameter indicating a change in the average color is set as the feature data. A parameter indicating the change in the average color is acquired by determining an image to have changed in color if a proportion of a change (a change in an R component or G component) in average color with respect to a preceding image is equal to or greater than a predetermined value, and counting the number of images that have changed in color between the first feature image to the second feature image (that is, the number of times the color has changed). It is considered that there is a possibility that a certain abnormality has occurred in a region that severely changes in color in the subject 10. Therefore, if a difference between a parameter calculated as a present feature data and a parameter calculated as a past feature data is large, it can be said that at a site in the subject 10 corresponding to these images, there is a possibility that a certain abnormality has newly been generated or an abnormality has vanished.

(3) Statistic of Parameter Indicating Presence or Absence of Particular Shape

A matching process having a particular shape as a template is performed on each image between the first feature image and the second feature image, and a statistic (an average value, a mode value, or the like) of a parameter such as a matching degree or the like acquired thereby is set as the feature data. When this is done, by treating the particular shape to be detected as a shape representing a particular lesion, a state of progress or the like of that lesion between a past examination and a present examination is able to be grasped.

(4) Number of Lesion Images (Images or the Like Extracted by Red Color Detection Process)

The number of lesion images extracted between the first feature image and the second feature image is set as the feature data. If a difference between the number of lesion images calculated as the present feature data and the number of the lesion images calculated as the past feature data is large, it can be said that there is a possibility that a certain change has occurred in that lesion between the past examination and the present examination.

(5) Movement Distance of Capsule Endoscope 2

A movement distance of the capsule endoscope 2 between the first feature image and the second feature image is set as the feature data. The movement distance of the capsule endoscope 2 is able to be estimated from a track sequentially connected of positions of the capsule endoscope 2 at imaging times of respective images. If a difference between a movement distance estimated as the present feature data and a movement distance estimated as the past feature data is large, it can be said that there is a possibility that a certain change has occurred in a shape (expansion, contraction, or the like) or position of a site (for example, a small intestine) in the subject 10 corresponding to these images.

(6) Time Period for which Capsule Endoscope 2 was Stopped

A time period, for which the capsule endoscope 2 was stopped between the first feature image and the second feature image, is set as the feature data. A stop time period of the capsule endoscope 2 is able to be estimated from, for example, the number of images having similarities with respect to their preceding images equal to or greater than a predetermined value (for example, 99%). If a difference between the stop time period acquired as the present feature data and the stop time period acquired as the last feature data is large, it can be said that there is a possibility that a factor (a tumor, a change in shape, retention of a residue, or the like) that inhibits movement of the capsule endoscope 2 has been newly generated or has vanished, at a site in the subject 10 corresponding to these images.

(7) Number of Times Capsule Endoscope 2 Stopped

The number of times the capsule endoscope 2 stopped between the first feature image and the second feature image is set as the feature data. The number of times the capsule endoscope 2 stopped is able to be determined by, for example, the number of images having similarities to their preceding images that are equal to or greater than a predetermined value (for example, 99%) and having change rates of the similarities that are equal to or greater than a predetermined value. If a difference between the number of stops acquired as the present feature data and the number of stops acquired as the previous feature data is large, it can be said that there is a possibility that a factor inhibiting movement of the capsule endoscope 2 has been newly generated or has vanished.

(8) Maximum Moving Speed of Capsule Endoscope 2

A maximum value of a moving speed of the capsule endoscope 2 between the first feature image and the second feature image is set as the feature data. The moving speed of the capsule endoscope 2 is able to be estimated by imaging times of images adjacent to each other in a time series and a positional change of the capsule endoscope 2. If a difference between the maximum moving speed acquired as the present feature data and the maximum moving speed acquired as the past feature data is large, it can be said that there is a possibility that a factor that changes a speed of the capsule endoscope 2 has been generated.

(9) Number of Rotations of Capsule Endoscope 2

The number of times the capsule endoscope 2 rotated between the first feature image and the second feature image is set as the feature data. Rotations of the capsule endoscope 2 are able to be estimated from the detection signal of the acceleration of the capsule endoscope 2, which is the related information of the image data. If a difference between the number of rotations acquired as the present feature data and the number of rotations acquired as the past feature data is large (if there is a large increase), it can be said that there is a possibility that a factor that inhibits advancement of the capsule endoscope 2 and rotates the capsule endoscope 2 at that place has been generated.

Figure 14:
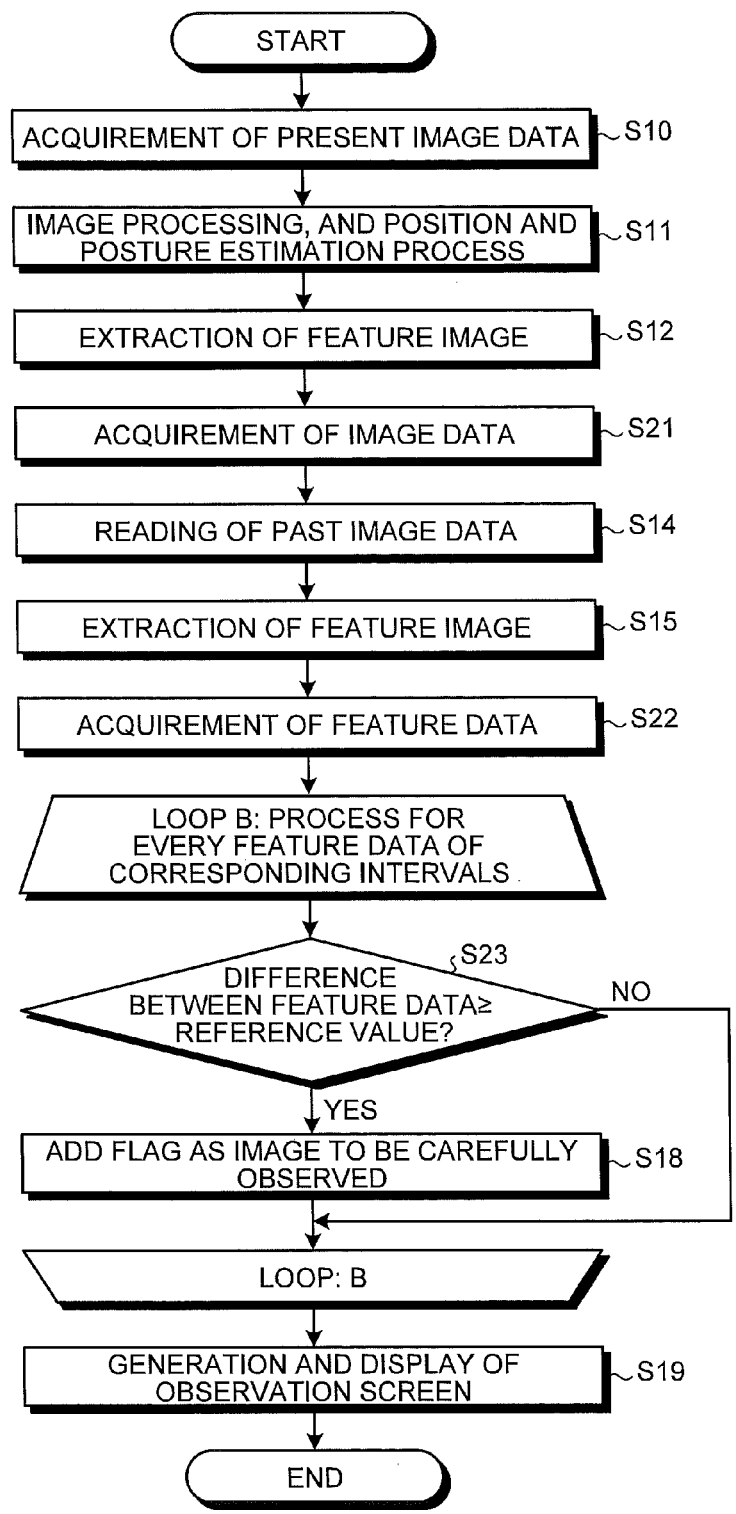
FIG. 14 is a flow chart illustrating operations of the image processing apparatus illustrated in FIG. 13.

Next, operations of the image processing apparatus 5-2 will be described. FIG. 14 is a flow chart illustrating the operations of the image processing apparatus 5-2. As illustrated in FIG. 14, in the second embodiment, only operations at steps S21, S22, and S23 are different from those of the first embodiment (see FIG. 4).

At step S21 subsequent to step S12, the feature data acquiring unit 54f acquires present feature data from the present image group.

Further, at step S22 subsequent to step S15, the feature data acquiring unit 54f acquires past feature data from the past image group.

Thereafter, the comparing unit 54e performs a process of a loop "B" for every image intervals corresponding to each other between the present image group and the past image group (the intervals between the first feature images and the second feature images). That is, if a difference between the present feature data and the past feature data is equal to or greater than a predetermined reference value (step S23: Yes), the careful observation flag is added to a series of images included in that image interval of the present image group (step S18).

Operations (step S19) thereafter are similar to those of the first embodiment.

As described above, according to the second embodiment, based on the quantity characterizing the movement of the capsule endoscope 2 calculated in the interval of the feature images corresponding between the present image group and the past image group, the images to be carefully observed are identified, and these images are displayed so as to attract the user's attention on the observation screen. Therefore, the user is able to intensively observe the images of the region in the subject having the possibility of having a certain change occurring during the period between the past examination and the present examination, and an observation efficiency is able to be improved.

Third Embodiment

Next, a third embodiment of the present invention will be described.

The third embodiment is characterized in that a user is able to select, as a feature image, a desired image from a present image group.

Figure 15:
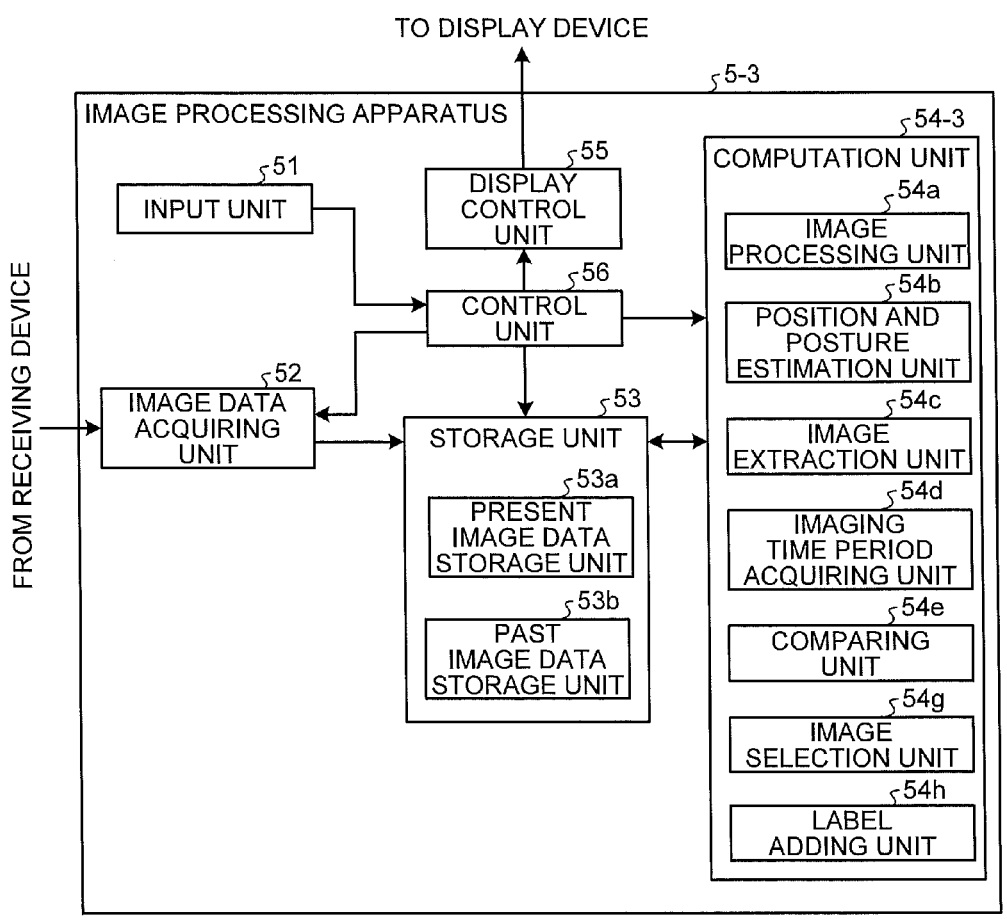
FIG. 15 is a block diagram illustrating a schematic configuration of an image processing apparatus according to a third embodiment of the present invention.

FIG. 15 is a block diagram illustrating a schematic configuration of an image processing apparatus according to a third embodiment of the present invention. As illustrated in FIG. 15, an image processing apparatus 5-3 according to the third embodiment includes a computation unit 54-3 further having an image selection unit 54g and a label adding unit 54h, in contrast to the image processing apparatus 5 illustrated in FIG. 3. A configuration of the computation unit 54-3 and the whole image processing apparatus 5-3 other than the image selection unit 54g and the label adding unit 54h is similar to that illustrated in FIG. 3.

The image selection unit 54g receives input of a selection signal corresponding to manipulation of the user using the input unit 51, and selects an image corresponding to the selection signal from the present image group and adds a selection flag thereto. Hereinafter, the image selected according to the user's manipulation from the present image group is referred to as "marking image".

The input of the selection signal is executed, for example, according to predetermined pointer operations on the observation screens D1 to D6 exemplified in FIG. 6 to FIG. 12, for example. Specifically, it may be a click operation on the image $M_{main}$ being displayed in the main display area d3 illustrated in FIG. 6, may be an operation on the capture button d5, or may be a click operation on a desired present image $M_i$ illustrated in FIG. 11.

The label adding unit 54h adds, when the marking image is selected from the present image group, a label representing a feature of the marking image. Examples of type of labels include labels representing features distinguishable as landmarks in the subject 10, such as an entrance of a stomach, a pylorus, a duodenal bulb, a eater's papilla, a Peyer patch, or a Bauhin's valve, and a location where a clip is placed, and labels representing symptoms of lesions such as a tumor and bleeding.

When this is done, the label adding unit 54h may add the label based on the feature detection information generated as a result of the image processing by the image processing unit 54a. Or, the label adding unit 54h may add the label based on an input signal according to the user's manipulation using the input unit 51. In that case, the input signal received by the label adding unit 54h may be text information input from the input device such as the key board, or the selection signal selected according to the user's operation using the input unit 51 from a predetermined plurality of label candidates. In the latter case, when the user performs a selection operation of the marking image, icons indicating text information or marks corresponding to the above described features are preferably displayed on the screen to allow the user to make the selection using the input device such as the mouse.

Further, in the third embodiment, the image extraction unit 54c extracts, based on the label added to the marking image, an image added with the same label from the past image group.

Next, operations of the image processing apparatus 5-3 will be described. FIG. 16 is a flow chart illustrating the operations of the image processing apparatus 5-3. As illustrated in FIG. 16, in the third embodiment, only operations at steps S31 and S32 are different from those of the first embodiment (see FIG. 4).

At step S31 subsequent to step S11, the image selection unit 54g adds, according to the marking operation by the user using the input unit 51, the selection flag and the label to the marking image.

At subsequent step S13, the imaging time period acquiring unit 54d treats the marking images extracted based on the selection flag as feature images and acquires an imaging time period between these images.

At step S32 subsequent to step S14, the image extraction unit 54c extracts, based on the label added to the marking image, a past image corresponding to the marking image from the past image group.

Operations thereafter (step S16 and thereafter) are similar to those of the first embodiment.

As described above, according to the third embodiment, of the present image group, the image determined by the user to be taken notice of is treated as the feature image and the imaging time period is compared with that of the past image group, and thus, the user is able to intensively observe, near the image the user is concerned with, an image having a possibility of having a certain change since the past examination.

In the third embodiment, although the user selects the marking image, instead of the image extraction unit 54c automatically extracting the feature image from the present image group (see step S12 of FIG. 4), both of the automatic extraction of the feature image by the image extraction unit 54c and the selection of the marking image by the user may be performed.

Further, the image selection unit 54g and the label adding unit 54h may be additionally provided in the computation unit 54-2 illustrated in FIG. 13.

Modified Example 3-1

Next, a modified example 3-1 of the third embodiment of the present invention will be described.

In the above described third embodiment, the extraction of the past image corresponding to the marking image is performed based on the label added to the marking image. However, the extraction of the past image may be performed by a method exemplified below.

In one example, first, the image selection unit 54g calculates, with respect to the present image group, imaging times of the marking images, with reference to an examination start time. The image selection unit 54g narrows down, from the past image group, to a plurality of past images having about the same imaging times as the imaging times of the marking images. When this is done, for the past image group also, the imaging times with reference to an examination start time are used. Thereafter, from the plurality of images narrowed down by the imaging times, images that were added with a selection flag during a past observation are extracted.

In another example, the image selection unit 54g may extract, from the plurality of past images narrowed down by the imaging times as described above, images that were captured during the past observation.

In yet another example, the image selection unit 54g may performs similar image determination process on the plurality of past images narrowed down by the imaging times and extract past images having highest similarities to the marking images.

Or, the image selection unit 54g may calculate a parameter indicating a predetermined feature (an abnormal site or the like) from the marking image, and by referring to the parameter, may extract a past image corresponding to the marking image, from the plurality of past images narrowed down by the imaging times.

Modified Example 4

Next, a modified example 4 of the first to third embodiments of the present invention will be described.

This modified example 4 is characterized in that on an observation screen based on a result of a present examination, information related to a past examination is displayed as a reference. This modified example 4 may be applied to any of the image processing apparatuses 5, 5-2, and 5-3 illustrated in FIG. 3, FIG. 13, and FIG. 15.

FIG. 17 is a schematic diagram illustrating an observation screen in the modified example 4. On an observation screen D7 illustrated in FIG. 17, in addition to the observation screen D2 illustrated in FIG. 7, a previous result button d25 and a previous result display area d26 are provided further.

The previous result button d25 is a button for a user to input an instruction to display a result of a past examination on the observation screen D7. According to a pointer operation on this previous result button d25, switch-over of display/non-display of the previous result display area d26 is possible.

The previous result display area d26 is an area in which an examination date of the past examination, and various required time periods or the like calculated based on imaging times of past images selected by the image selection unit 54g. Specifically, information is displayed, such as: a time period required to reach a stomach (time period to reach stomach); a time period required to pass through the stomach (time period to pass through stomach); a time period required to reach a small intestine (time period to reach small intestine); and a time period required to pass through the small intestine (time period to pass through small intestine), which are from a time point at which the capsule endoscope 2 is swallowed by the subject 10. Each of these time periods is calculated from an imaging time of each image, with reference to a swallowing time of the capsule endoscope 2 (examination start time), but for example, it may be calculated with reference to an imaging start time (an imaging time of a first image) or a pylorus passage time (a stomach arrival time).

Further, in the previous result display area d26, in addition to the above listed times, a number of captured images, a label added to the captured images, or an observation result (findings) input by a user may be displayed further. Further, each of these items may be set by the user to be customized.

As described above, according to the modified example 4, since detailed information in the past examination is displayed on the screen as textual information, the user is able to grasp differences between the past examination and a present examination without separately referring to records of the past examination.

The previous result display area d26 may be displayed on the observation screen D7 only when there is a difference equal to or greater than a predetermined reference value in imaging time periods (or feature data) corresponding between the present image group and the past image group. Or, the previous result display area d26 may be settable to be always displayed at any position on the observation screen D7.

Modified Example 5

Next, a modified example 5 of the first to third embodiments of the present invention will be described.

On the observation screens D2 to D4 and D6 described in the first embodiment, the past images are extracted based on the present image being displayed and are displayed in the past image display area d12 or D15, or the past image list display area d22. However, by searching through the present image group based on a particular past image, a present image to be displayed in the main display area d3 or the present image list display area d21 may be extracted.

For example, if a past image is present, which has been determined to be an abnormal site by a user and added with a label indicating that there is the abnormal site (hereinafter, referred to as "abnormal label") during a past observation on a past image group, the image extraction unit 54c may extract, from a present image group, a present image corresponding to the past image added with the abnormal label.

A method of this extraction to be used may be, for example, a method of, based on imaging times of past images with reference to an examination start time (or a pylorus passage time), narrowing down to present images having close imaging times, and thereafter performing a similar image determination process to select a present image having a highest similarity to the past image. When this is done, instead of the similarity of the whole image, a similarity only with respect to a site where an abnormality is present may be calculated. Or, after narrowing down the present images based on the imaging times, a present image may be extracted using a parameter representing a feature (for example, an abnormal site or the like) similar to that of the past image. In addition, based on positional information of the past images, a present image having positional information close thereto may be extracted.

The display control unit 55 displays the present image extracted as described above on the observation screen in the format of attracting the user's attention. For example, if the present images are displayed as a pseudo moving image in the main display area d3, a display frame rate may be decreased to perform the display slowly when the time to display the present image corresponding to the past image added with the abnormal label comes. Further, a screen may be generated, in which a list of only the present images corresponding to the past images added with the abnormal label are displayed.

Furthermore, to the time bar d7 (for example, see FIG. 6) or an average color bar d16 (see FIG. 9), a mark may be added in or blinking display may be performed for an area of the present image extracted correspondingly with the past image added with the abnormal label.

According to the above described modified example 5, since the present image corresponding to the past image added with the abnormal label in the past is displayed in the format of attracting the user's attention, the user is able to intensively observe the progress of the site diagnosed to be abnormal in the past.

Modified Example 6

Next, a modified example 6 of the first to third embodiments of the present invention will be described.

In the first to third embodiments, the case in which the past examination has been performed only once has been described. However, if the same subject 10 has been examined plural times in the past, extraction and display of past images are preferably performed as described below.

If a recent state of the subject 10 is to be diagnosed, of the plural past examinations, image extraction is preferably performed targeted only to a past image group acquired by a newest examination.

On the contrary, if a pattern of change in state of the subject 10 is to be diagnosed, image extraction from each of past image groups of the plural examinations is preferably performed. In this case, the past images extracted from respective past image groups may be sequentially switched over for display in the past image display area d12 illustrated in FIG. 7 or the past image display area d15 illustrated in FIG. 8 and FIG. 9, for example. Further, a plurality of past image display areas d15 may be provided on one screen, and a plurality of past images corresponding to the feature images extracted from the present image group (or the marking images) may be displayed being arranged in time series. In this case, the average color bars d16 and d17 illustrated in FIG. 9 may be provided according to the number of examinations and displayed being arranged in time series. Or, the track display area d18 illustrated in FIG. 10 may be provided according to the number of examinations and displayed being arranged in time series.

Further, as described in the modified example 4, if the previous result display area d26 is to be provided on the observation screen, an average value of results of several past examinations may be displayed, or the previous result display area d26 may be provided for each of the past examinations and displayed being arranged in time series on the single observation screen.

Modified Example 7

Next, a modified example 7 of the first to third embodiments of the present invention will be described.

Although in the first to third embodiments, the past image data are stored in the built-in storage units 53 of the image processing apparatuses 5, 5-2, and 5-3, the past image data may be stored in an external storage device connectable to the image processing apparatuses 5, 5-2, and 5-3. Or, the past image data may be stored in a server or the like, and the past image data may be fetched into the image processing apparatuses 5, 5-2, and 5-3 via a network such as a wire or wireless LAN.

As described above, according to the first to third embodiments of the present invention and the modified examples thereof, the imaging time period or feature data acquired from the image group of the present examination is compared with the imaging time period or feature data acquired from the image group of the past examination, and if the difference therebetween is equal to or greater than the reference value, the display control based on the result of the comparison is performed on the image group of the present examination, and thus observation utilizing a result of a past examination becomes possible. Thereby, a discovery efficiency of an abnormal site is able to be increased and an observation time period is able to be shortened.

The above described present invention is not limited to the first to third embodiments and the modified examples thereof, and various inventions may be formed by combining as appropriate a plurality of structural elements disclosed in the respective embodiments and modified examples. For example, formation by excluding some of the structural elements from the whole structural elements illustrated in the respective embodiments and modified examples may be made, or formation by combining as appropriate the structural elements illustrated in the different embodiments and modified examples may be made.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A image processing apparatus that processes an image of inside of a subject, the image acquired by a capsule endoscope that is introduced into the subject and captures images of the inside of the subject, the image processing apparatus comprising:
    an image extraction unit that extracts, from a first image group acquired by sequentially capturing images of the inside of the subject by the capsule endoscope images of the inside of the subject, a first feature image representing a first feature and a second feature image representing a second feature, and that further extracts, from a second image group acquired before the first image group by sequentially capturing images of the inside of a subject identical to the subject, a third feature image representing the first feature and a fourth feature image representing the second feature;
    a feature data acquiring unit that acquires, a first feature data characterizing a movement of the capsule endoscope between the first feature image and the second feature image extracted from the first image group, and a second feature data characterizing a movement of the capsule endoscope between the third feature image and the fourth feature image extracted from the second image group;
    a comparing unit that compares the first feature data with the second feature data; and
    a display control unit that performs, with respect to the first image group, display control based on a result of the comparison by the comparing unit.

2. The image processing apparatus according to claim 1, wherein the display control unit performs control of displaying, as images to be carefully observed, a series of images between the first feature image and the second feature image of the first image group.

3. The image processing apparatus according to claim 1, further comprising an image processing unit that performs predetermined image processing on a series of images between the first feature image and the second feature image of the first image group.

4. The image processing apparatus according to claim 1, further comprising:
an image data acquiring unit that acquires image data corresponding to the first image group;
a storage unit that stores therein the second image group; and
an image processing unit that performs image processing of detecting the first and second features, with respect to each of the first and second image groups.

5. The image processing apparatus according to claim 1, further comprising:
an image selection unit that selects, based on a selection signal input from outside, an image from the first image group,
wherein the image extraction unit extracts an image corresponding to the image selected by the image selection unit, from the second image group.

6. The image processing apparatus according to claim 1, wherein the first and second feature data are a time period between an imaging time of the first feature image and an imaging time of the second feature image and a time period between an imaging time of the third feature image and an imaging time of the fourth feature image, respectively.

7. The image processing apparatus according to claim 1, wherein the first and second feature data are the number of images captured by the capsule endoscope between an imaging time of the first feature image and an imaging time of the second image and the number of images captured by the capsule endoscope between an imaging time of the third feature image and an imaging time of the fourth feature image, respectively.

8. The image processing apparatus according to claim 1, wherein the first and second feature data are a statistic of a parameter representing an average color of a series of images between the first feature image and the second feature image or a parameter indicating a change in the average color and a statistic of a parameter representing an average color of a series of images between the third feature image and the fourth feature image or a parameter indicating a change in the average color, respectively.

9. The image processing apparatus according to claim 1, wherein the first and second feature data are a statistic of a parameter indicating presence or absence of a particular shape in each of a series of images between the first feature image and the second feature image and a statistic of a parameter indicating presence or absence of a particular shape in each of a series of images between the third feature image and the fourth feature image, respectively.

10. The image processing apparatus according to claim 1, wherein the first and second feature data are the number of lesion images detected from a series of images between the first feature image and the second feature image and the number of lesion images detected from a series of images between the third feature image and the fourth feature image, respectively.

11. The image processing apparatus according to claim 1, wherein the first and second feature data are a parameter representing a movement of the capsule endoscope between an imaging time of the first feature image and an imaging time of the second feature image and a parameter representing a movement of the capsule endoscope between an imaging time of the third feature image and an imaging time of the fourth feature image, respectively.

12. The image processing apparatus according to claim 11, wherein the parameter indicating the movement of the capsule endoscope is any one of: a movement distance of the capsule endoscope; the number of times the capsule endoscope stopped; a time period for which the capsule endoscope was stopped; a maximum moving speed of the capsule endoscope; and the number of rotations of the capsule endoscope.

13. An image processing method of processing an image of inside of a subject, the image acquired by a capsule endoscope that is introduced into the subject and that captures images of the inside of the subject, the method comprising:
extracting a first feature image representing a first feature and a second feature image representing a second feature from a first image group acquired by sequentially capturing images of the inside of the subject by the capsule endoscope, and further extracting a third feature image representing the first feature and a fourth feature image representing the second feature from a second image group acquired before the first image group by sequentially capturing images of the inside of the subject;
acquiring a first feature data characterizing a movement of the capsule endoscope between the first feature image and the second feature image extracted from the first image group, and a second feature data characterizing a movement of the capsule endoscope between the third feature image and the fourth feature image extracted from the second image group;
comparing the first feature data with the second feature data; and
performing, with respect to the first image group, display control based on a result of the comparison by the comparing.

* * * * *